US008273324B2

(12) United States Patent
Rioux et al.

(10) Patent No.: US 8,273,324 B2
(45) Date of Patent: *Sep. 25, 2012

(54) EMBOLIZATION (75) Inventors: Robert F. Rioux, Ashland, MA (US); Thomas V. Casey, II, Grafton, MA (US); Janel Lanphere, Flagstaff, AZ (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/190,823

(22) Filed: Jul. 26, 2011

(65) Prior Publication Data
US 2011/0280947 A1 Nov. 17, 2011

Related U.S. Application Data (63) Continuation of application No. 10/651,475, filed on Aug. 29, 2003, now Pat. No. 8,012,454, which is a continuation-in-part of application No. 10/232,265, filed on Aug. 30, 2002, now Pat. No. 7,462,366.

(51) Int. Cl.
*A61K 9/14* (2006.01)
*A61K 51/00* (2006.01)
(52) U.S. Cl. .......... 424/1.11; 424/488; 424/489
(58) Field of Classification Search ............. 424/1.11, 424/129, 450, 489
See application file for complete search history.

(56) References Cited

U.S. PATENT DOCUMENTS

| 2,275,154 A | 3/1942 | Merrill et al. |
| 2,609,347 A | 9/1952 | Wilson |
| 3,663,470 A | 5/1972 | Nishimura et al. |
| 3,737,398 A | 6/1973 | Yamaguchi |
| 3,957,933 A | 5/1976 | Egli et al. |
| 4,025,686 A | 5/1977 | Zion |
| 4,055,377 A | 10/1977 | Erickson et al. |
| 4,076,640 A | 2/1978 | Forgensi et al. |
| 4,098,728 A | 7/1978 | Rosenblatt |
| 4,110,529 A | 8/1978 | Stoy |
| 4,191,672 A | 3/1980 | Salome et al. |
| 4,198,318 A | 4/1980 | Stowell et al. |
| 4,243,794 A | 1/1981 | White et al. |
| 4,246,208 A | 1/1981 | Dundas |
| 4,266,030 A | 5/1981 | Tschang et al. |
| 4,268,495 A | 5/1981 | Muxfeldt et al. |
| 4,271,281 A | 6/1981 | Kelley et al. |
| 4,413,070 A | 11/1983 | Rembaum |
| 4,427,794 A | 1/1984 | Lange et al. |
| 4,428,869 A | 1/1984 | Munteanu et al. |
| 4,429,062 A | 1/1984 | Pasztor et al. |
| 4,442,843 A | 4/1984 | Rasor et al. |
| 4,444,961 A | 4/1984 | Timm |
| 4,452,773 A | 6/1984 | Molday |
| 4,456,693 A | 6/1984 | Welsh |
| 4,459,145 A | 7/1984 | Elsholz |
| 4,472,552 A | 9/1984 | Blouin |
| 4,477,255 A | 10/1984 | Pasztor et al. |
| 4,492,720 A | 1/1985 | Mosier |
| 4,515,906 A | 5/1985 | Friesen et al. |
| 4,522,953 A | 6/1985 | Barby et al. |
| 4,542,178 A | 9/1985 | Zimmermann et al. |
| 4,551,132 A | 11/1985 | Pasztor et al. |
| 4,551,436 A | 11/1985 | Johnson et al. |
| 4,573,967 A | 3/1986 | Hargrove et al. |
| 4,622,362 A | 11/1986 | Rembaum |
| 4,623,706 A | 11/1986 | Timm et al. |
| 4,629,464 A | 12/1986 | Takata et al. |
| 4,657,756 A | 4/1987 | Rasor et al. |
| 4,661,137 A | 4/1987 | Garnier et al. |
| 4,663,358 A | 5/1987 | Hyon et al. |
| 4,671,954 A | 6/1987 | Goldberg et al. |
| 4,671,994 A | 6/1987 | Cochran, Jr. |
| 4,675,113 A | 6/1987 | Graves et al. |
| 4,678,710 A | 7/1987 | Sakimoto et al. |
| 4,678,814 A | 7/1987 | Rembaum |
| 4,680,320 A | 7/1987 | Uku et al. |
| 4,681,119 A | 7/1987 | Rasor et al. |
| 4,695,466 A | 9/1987 | Morishita et al. |
| 4,742,086 A | 5/1988 | Masamizu et al. |
| 4,743,507 A | 5/1988 | Franses et al. |
| 4,772,635 A | 9/1988 | Mitschker et al. |
| 4,782,097 A | 11/1988 | Jain et al. |
| 4,789,501 A | 12/1988 | Day et al. |
| 4,795,741 A | 1/1989 | Leshchiner et al. |
| 4,801,458 A | 1/1989 | Hidaka et al. |
| 4,804,366 A | 2/1989 | Zdeb et al. |
| 4,819,637 A | 4/1989 | Dormandy, Jr. et al. |
| 4,822,535 A | 4/1989 | Ekman et al. |
| 4,833,237 A | 5/1989 | Kawamura et al. |
| 4,850,978 A | 7/1989 | Dudar et al. |

(Continued)

FOREIGN PATENT DOCUMENTS

CA 2326977 10/1999

(Continued)

OTHER PUBLICATIONS

U.S. Appl. No. 11/274,538, filed Nov. 15, 2005, Tenney et al.
Bachtsi, A.R. et al., "An Experimental Investigation of Enzyme Release from Poly(vinyl alcohol) crosslinked Microspheres", *J. Microencapsulation*, vol. 12, No. 1, pp. 23-35; 1995.
Barr, J.D., et al.,"polyvinyl Alcohol Foam Particles Sizes and Concentrations Injectable through Microcatheters", *JVIR*, vol. 9, No. 1, pp. 113-118; 1998.
Barton, P. et al., "Embolization of Bone Metastases", *Journal of Vascular and Interventional Radiology*, vol. 7, No. 1, Jan.-Feb. 1996, p. 81-88.
Barttinelli, L. et al., "New Class of Poly(vinyl alcohol) Polymrs as Column—Chromatography Stationary Phases for Candida Rugosa Lipase Isoforms Separation.", *J. Chromatogr A*, vol. 753, No. 1, pp. 47-55; 1996. Abstract. http://www.ncbi.nlm.nih.gov/entrez/query.fcgi?
Beaujeux, R. et al., "Trisacryl Gelatin Microspheres for Therapeutic Embolization, II: Preliminary Clinical Evaluation in Tumors and Arteriovenous Malformations," *AJNR Am. J. Neuroradiol.* 17:541-548, Mar. 1996.

(Continued)

*Primary Examiner* — Michael G Hartley
*Assistant Examiner* — Jagadishwar Samala
(74) *Attorney, Agent, or Firm* — Bingham McCutchen LLP (57) ABSTRACT

A particle includes a ferromagnetic material, a radiopaque material, and/or an MRI-visible material.

20 Claims, 5 Drawing Sheets

U.S. PATENT DOCUMENTS

| | | | |
|---|---|---|---|
| 4,859,711 A | 8/1989 | Jain et al. |
| 4,863,972 A | 9/1989 | Itagaki et al. |
| 4,929,400 A | 5/1990 | Rembaum et al. |
| 4,933,372 A | 6/1990 | Feibush et al. |
| 4,938,967 A | 7/1990 | Newton et al. |
| 4,954,399 A | 9/1990 | Tani et al. |
| 4,970,062 A | 11/1990 | Atcher et al. |
| 4,981,625 A | 1/1991 | Rhim et al. |
| 4,990,340 A | 2/1991 | Hidaka et al. |
| 4,999,188 A | 3/1991 | Sloldovnik et al. |
| 5,007,940 A | 4/1991 | Berg |
| 5,011,677 A | 4/1991 | Day et al. |
| H915 H | 5/1991 | Gibbs |
| 5,032,117 A | 7/1991 | Motta |
| 5,034,324 A | 7/1991 | Shinozaki et al. |
| 5,047,438 A | 9/1991 | Feibush et al. |
| 5,079,274 A | 1/1992 | Schneider et al. |
| 5,106,903 A | 4/1992 | Vanderhoff et al. |
| 5,114,421 A | 5/1992 | Polak |
| 5,116,387 A | 5/1992 | Berg |
| 5,120,349 A | 6/1992 | Stewart et al. |
| 5,125,892 A | 6/1992 | Drudik |
| 5,147,631 A | 9/1992 | Glajch et al. |
| 5,147,937 A | 9/1992 | Frazza et al. |
| 5,149,543 A | 9/1992 | Cohen et al. |
| 5,158,573 A | 10/1992 | Berg |
| 5,171,214 A | 12/1992 | Kolber et al. |
| 5,171,217 A | 12/1992 | March et al. |
| 5,190,766 A | 3/1993 | Ishihara |
| 5,202,352 A | 4/1993 | Okada et al. |
| 5,216,096 A | 6/1993 | Hattori et al. |
| 5,236,410 A | 8/1993 | Granov et al. |
| 5,253,991 A | 10/1993 | Yokota et al. |
| 5,260,002 A | 11/1993 | Wang |
| 5,262,176 A | 11/1993 | Palmacci et al. |
| 5,288,763 A | 2/1994 | Li et al. |
| 5,292,814 A | 3/1994 | Bayer et al. |
| 5,302,369 A | 4/1994 | Day et al. |
| 5,314,974 A | 5/1994 | Ito et al. |
| 5,316,774 A | 5/1994 | Eury et al. |
| 5,344,452 A | 9/1994 | Lemperle |
| 5,344,867 A | 9/1994 | Morgan et al. |
| 5,349,957 A | 9/1994 | Yudelson |
| 5,354,290 A | 10/1994 | Gross |
| 5,369,133 A | 11/1994 | Ihm et al. |
| 5,369,163 A | 11/1994 | Chiou et al. |
| 5,382,260 A | 1/1995 | Dormandy, Jr. et al. |
| 5,384,124 A | 1/1995 | Courteille et al. |
| 5,397,303 A | 3/1995 | Sancoff et al. |
| 5,398,851 A | 3/1995 | Sancoff et al. |
| 5,403,870 A | 4/1995 | Gross |
| 5,417,982 A | 5/1995 | Modi |
| 5,431,174 A | 7/1995 | Knute |
| 5,435,645 A | 7/1995 | Faccioli et al. |
| 5,441,746 A | 8/1995 | Chagnon |
| 5,456,693 A | 10/1995 | Conston et al. |
| 5,468,801 A | 11/1995 | Antonelli et al. |
| 5,469,854 A | 11/1995 | Unger et al. |
| 5,476,472 A | 12/1995 | Dormandy, Jr. et al. |
| 5,484,584 A | 1/1996 | Wallace et al. |
| 5,490,984 A | 2/1996 | Freed |
| 5,494,682 A | 2/1996 | Cohen et al. |
| 5,494,940 A | 2/1996 | Unger et al. |
| 5,512,604 A | 4/1996 | Demopolis |
| 5,514,090 A | 5/1996 | Kriesel et al. |
| 5,514,379 A | 5/1996 | Weissleder et al. |
| 5,525,334 A | 6/1996 | Ito et al. |
| 5,534,589 A | 7/1996 | Hager et al. |
| 5,541,031 A | 7/1996 | Yamashita et al. |
| 5,542,935 A | 8/1996 | Unger et al. |
| 5,553,741 A | 9/1996 | Sancoff et al. |
| 5,556,391 A | 9/1996 | Cercone et al. |
| 5,556,610 A | 9/1996 | Yan et al. |
| 5,558,255 A | 9/1996 | Sancoff et al. |
| 5,558,822 A | 9/1996 | Gitman et al. |
| 5,558,856 A | 9/1996 | Klaveness et al. |
| 5,559,266 A | 9/1996 | Klaveness et al. |
| 5,567,415 A | 10/1996 | Porter |
| 5,569,193 A | 10/1996 | Hofstetter et al. |
| 5,569,449 A | 10/1996 | Klaveness et al. |
| 5,569,468 A | 10/1996 | Modi |
| 5,571,182 A | 11/1996 | Ersek et al. |
| 5,580,575 A | 12/1996 | Unger et al. |
| 5,583,162 A | 12/1996 | Li et al. |
| 5,585,112 A | 12/1996 | Unger et al. |
| 5,595,821 A | 1/1997 | Hager et al. |
| 5,622,657 A | 4/1997 | Takada et al. |
| 5,624,685 A | 4/1997 | Takahashi et al. |
| 5,635,215 A | 6/1997 | Boschetti et al. |
| 5,637,087 A | 6/1997 | O'Neil et al. |
| 5,639,710 A | 6/1997 | Lo et al. |
| 5,648,095 A | 7/1997 | Illum et al. |
| 5,648,100 A | 7/1997 | Boschetti et al. |
| 5,650,116 A | 7/1997 | Thompson |
| 5,651,990 A | 7/1997 | Takada et al. |
| 5,653,922 A | 8/1997 | Li et al. |
| 5,657,756 A | 8/1997 | Vrba |
| 5,681,576 A | 10/1997 | Henry |
| 5,695,480 A | 12/1997 | Evans et al. |
| 5,695,740 A | 12/1997 | Porter |
| 5,698,271 A | 12/1997 | Liberti et al. |
| 5,701,899 A | 12/1997 | Porter |
| 5,715,824 A | 2/1998 | Unger et al. |
| 5,716,981 A | 2/1998 | Hunter et al. |
| 5,718,884 A | 2/1998 | Klaveness et al. |
| 5,723,269 A | 3/1998 | Akagi et al. |
| 5,725,534 A | 3/1998 | Rasmussen |
| 5,746,734 A | 5/1998 | Dormandy, Jr. et al. |
| 5,752,974 A | 5/1998 | Rhee et al. |
| 5,760,097 A | 6/1998 | Li et al. |
| 5,766,147 A | 6/1998 | Sancoff et al. |
| 5,770,222 A | 6/1998 | Unger et al. |
| 5,779,668 A | 7/1998 | Grabenkort |
| 5,785,642 A | 7/1998 | Wallace et al. |
| 5,785,682 A | 7/1998 | Grabenkort |
| 5,792,478 A | 8/1998 | Lawin et al. |
| 5,795,562 A | 8/1998 | Klaveness et al. |
| 5,797,953 A | 8/1998 | Tekulve |
| 5,807,323 A | 9/1998 | Kriesel et al. |
| 5,813,411 A | 9/1998 | Van Bladel et al. |
| 5,823,198 A | 10/1998 | Jones et al. |
| 5,827,502 A | 10/1998 | Klaveness et al. |
| 5,827,531 A | 10/1998 | Morrison et al. |
| 5,830,178 A | 11/1998 | Jones et al. |
| 5,833,361 A | 11/1998 | Funk |
| 5,846,518 A | 12/1998 | Yan et al. |
| 5,853,752 A | 12/1998 | Unger et al. |
| 5,855,615 A | 1/1999 | Bley et al. |
| 5,863,957 A | 1/1999 | Li et al. |
| 5,876,372 A | 3/1999 | Grabenkort et al. |
| 5,877,224 A | 3/1999 | Brocchini et al. |
| 5,885,216 A | 3/1999 | Evans, III et al. |
| 5,885,547 A | 3/1999 | Gray |
| 5,888,546 A | 3/1999 | Ji et al. |
| 5,888,930 A | 3/1999 | Smith et al. |
| 5,891,155 A | 4/1999 | Irie |
| 5,894,022 A | 4/1999 | Ji et al. |
| 5,895,411 A | 4/1999 | Irie |
| 5,899,877 A | 5/1999 | Leibitzki et al. |
| 5,902,832 A | 5/1999 | Van Bladel et al. |
| 5,922,025 A | 7/1999 | Hubbard |
| 5,922,304 A | 7/1999 | Unger |
| 5,928,626 A | 7/1999 | Klaveness et al. |
| 5,935,553 A | 8/1999 | Unger et al. |
| 5,951,160 A | 9/1999 | Ronk |
| 5,957,848 A | 9/1999 | Sutton et al. |
| 5,959,073 A | 9/1999 | Schlameus et al. |
| 5,964,797 A | 10/1999 | Ho |
| 6,003,566 A | 12/1999 | Thibault et al. |
| 6,015,546 A | 1/2000 | Sutton et al. |
| 6,027,472 A | 2/2000 | Kriesel et al. |
| 6,028,066 A | 2/2000 | Unger |
| 6,047,861 A | 4/2000 | Vidal et al. |
| 6,051,247 A | 4/2000 | Hench et al. |
| 6,059,766 A | 5/2000 | Greff |
| 6,063,068 A | 5/2000 | Fowles et al. |
| 6,071,495 A | 6/2000 | Unger et al. |

| | | | | | | |
|---|---|---|---|---|---|---|
| 6,071,497 | A | 6/2000 | Steiner et al. | JP | 6-218271 | 8/1994 |
| 6,073,759 | A | 6/2000 | Lamborne et al. | JP | 7/018357 | 1/1995 |
| 6,090,925 | A | 7/2000 | Woiszwillo et al. | JP | 9-110678 | 4/1997 |
| 6,096,344 | A | 8/2000 | Liu et al. | JP | 9-165328 | 6/1997 |
| 6,099,064 | A | 8/2000 | Lund | JP | 9-316271 | 12/1997 |
| 6,099,864 | A | 8/2000 | Morrison et al. | JP | 10-085224 | 4/1998 |
| 6,100,306 | A | 8/2000 | Li et al. | JP | 10/127754 | 5/1998 |
| 6,139,963 | A | 10/2000 | Fujii et al. | JP | 10-130329 | 5/1998 |
| 6,149,623 | A | 11/2000 | Reynolds | JP | 10-158075 | 6/1998 |
| 6,162,377 | A | 12/2000 | Ghosh et al. | JP | 10/337335 | 12/1998 |
| 6,165,193 | A | 12/2000 | Greene, Jr. et al. | JP | 11-92568 | 4/1999 |
| 6,167,313 | A | 12/2000 | Gray et al. | JP | 2002 017848 | 1/2002 |
| 6,191,193 | B1 | 2/2001 | Lee et al. | WO | WO 92/21327 | 12/1992 |
| 6,214,331 | B1 | 4/2001 | Vanderhoff et al. | WO | WO 93/00063 | 1/1993 |
| 6,214,384 | B1 | 4/2001 | Pallado et al. | WO | WO 93/19702 | 10/1993 |
| 6,224,630 | B1 | 5/2001 | Bao et al. | WO | WO 94/10936 | 5/1994 |
| 6,224,794 | B1 | 5/2001 | Amsden et al. | WO | WO 95/03036 | 2/1995 |
| 6,235,224 | B1 | 5/2001 | Mathiowitz et al. | WO | WO 95/22318 | 8/1995 |
| 6,238,403 | B1 | 5/2001 | Greene, Jr. et al. | WO | WO 96/37165 | 11/1996 |
| 6,251,661 | B1 | 6/2001 | Urabe et al. | WO | WO 96/39464 | 12/1996 |
| 6,258,338 | B1 | 7/2001 | Gray | WO | WO 98/04616 | 2/1998 |
| 6,261,585 | B1 | 7/2001 | Sefton et al. | WO | WO 98/10798 | 3/1998 |
| 6,264,861 | B1 | 7/2001 | Tavernier et al. | WO | WO98/47532 | 10/1998 |
| 6,267,154 | B1 | 7/2001 | Felicelli et al. | WO | WO 99/43380 | 2/1999 |
| 6,268,053 | B1 | 7/2001 | Woiszwillo et al. | WO | WO 99/12577 | 3/1999 |
| 6,277,392 | B1 | 8/2001 | Klein | WO | 99/51278 | 10/1999 |
| 6,291,605 | B1 | 9/2001 | Freeman et al. | WO | WO 99/51278 | 10/1999 |
| 6,306,418 | B1 | 10/2001 | Bley | WO | WO 99/57176 | 11/1999 |
| 6,306,427 | B1 | 10/2001 | Annonier et al. | WO | WO 00/23054 | 4/2000 |
| 6,315,709 | B1 | 11/2001 | Garibaldi et al. | WO | WO 00/40259 | 7/2000 |
| 6,335,384 | B1 | 1/2002 | Evans et al. | WO | 00/44287 | 8/2000 |
| 6,344,182 | B1 | 2/2002 | Sutton et al. | WO | 00/66183 | 9/2000 |
| 6,364,823 | B1 | 4/2002 | Garibaldi et al. | WO | WO 00/66183 | 11/2000 |
| 6,394,965 | B1 | 5/2002 | Klein | WO | WO 00/71196 | 11/2000 |
| 6,410,508 | B1 | 6/2002 | Isales et al. | WO | WO 00/74633 A2 | 12/2000 |
| 6,423,332 | B1 | 7/2002 | Huxel et al. | WO | 01/66016 | 9/2001 |
| 6,432,437 | B1 | 8/2002 | Hubbard | WO | WO 01/70291 A2 | 9/2001 |
| 6,544,544 | B2 | 4/2003 | Hunter et al. | WO | WO 01/76845 | 10/2001 |
| 6,565,887 | B1 | 5/2003 | Gray et al. | WO | WO 02/11696 A2 | 2/2002 |
| 6,586,364 | B2 | 7/2003 | Kubota et al. | WO | WO 02/34298 | 5/2002 |
| 6,602,524 | B2 | 8/2003 | Batich et al. | WO | WO 02/34299 | 5/2002 |
| 6,680,046 | B1 | 1/2004 | Boschetti | WO | WO 02/34300 | 5/2002 |
| 6,706,394 | B2 | 3/2004 | Kuehnle et al. | WO | WO 02/43580 A2 | 6/2002 |
| 6,777,001 | B1 | 8/2004 | Umezu et al. | WO | WO 03/013552 | 2/2003 |
| 6,998,137 | B2 | 2/2006 | Shih et al. | WO | WO03/082359 | 9/2003 |
| 7,074,175 | B2 * | 7/2006 | Handy et al. .............. 600/9 | WO | WO 2004/020042 | 3/2004 |
| 7,591,993 | B2 | 9/2009 | Boschetti | WO | WO 2004/040972 | 5/2004 |
| 8,012,454 | B2 * | 9/2011 | Rioux et al. .............. 424/1.11 | | | |
| 2001/0001835 | A1 | 5/2001 | Greene, Jr. et al. | | | |
| 2001/0016210 | A1 | 8/2001 | Mathiowitz et al. | | | |
| 2001/0036451 | A1 | 11/2001 | Goupil et al. | | | |
| 2001/0051670 | A1 | 12/2001 | Goupil et al. | | | |
| 2002/0054912 | A1 | 5/2002 | Kim et al. | | | |
| 2003/0163187 | A1 | 8/2003 | Weber | | | |
| 2003/0185896 | A1 | 10/2003 | Buiser et al. | | | |
| 2003/0215519 | A1 | 11/2003 | Schwarz et al. | | | |

FOREIGN PATENT DOCUMENTS

| | | |
|---|---|---|
| DE | 42 01 461 | 7/1993 |
| DE | 9414868.6 | 9/1994 |
| DE | 100 26 620 | 5/2000 |
| DE | 297 24 255 U1 | 10/2000 |
| EP | 0 422 258 A1 | 10/1989 |
| EP | 0 402 031 | 5/1990 |
| EP | 0 422 258 | 4/1991 |
| EP | 0 470 569 A1 | 2/1992 |
| EP | 0 547 530 B1 | 6/1993 |
| EP | 0 600 529 A | 12/1993 |
| EP | 0 623 012 B1 | 11/1994 |
| EP | 0 706 376 B1 | 4/1996 |
| EP | 0 730 847 A1 | 9/1996 |
| EP | 0 744 940 B1 | 12/1996 |
| EP | 0 797 988 A2 | 10/1997 |
| ES | 2 096 521 | 3/1997 |
| JP | 59-196738 | 11/1984 |
| JP | 62-45637 | 2/1987 |
| JP | 4-057836 | 2/1992 |
| JP | 4-74117 | 3/1992 |
| JP | 6-57012 | 3/1994 |

OTHER PUBLICATIONS

Berenstein, A. et al., "Catheter and Material Selection for Transarterial Embolization: Technical Considerations. II. Materials.", *Radiology*, vol. 132, No. 3, pp. 631-639; 1979.

Berenstein, A. et al., "Microembolization Techniques of Vascular Occlusion: Radiologic, Patohologic, and Clinical Correlation", *AJNR Am I Neuroradiol*, vol. 2, No. 3, pp. 261-267; 1981. Abstract, http://www.ncbi.nlm.nih.gov/entrez/query.fcgi.

Bruix, J. et al., "Transarterial Embolization Versus Symptomatic Treatment in Patients With Advanced Hepatocellular Carcinoma: Results of a Randomized, Controlled Trial in a Single Institution", Hepatology, Jun. 1998, vol. 27, No. 6, pp. 1578-1583 Available Web Site: http://www.hepatitis-central.com/hcv/hcc/embolization/references.html.

Buhle, Jr. EL, "Re: Re: Hepatic Arterial Embolization", UCLA Medicine Online, Available Web Site: http://www.meds.com/archive/mol-cancer/1996/msg00128.html.

Burczak, et al., "Long-term in vivo performance and biocompatibility of poly (vinyl alcohol) hydrogel macrocapsules for hybrid-type artificial pancreas", Biomaterials, vol. 17, No. 24, pp. 2351-2356, 1996, abs: http://www.ncbi.nlm.nih.gov/entrez/query.fcgi?cmd=retrieve&db=PubMed&list_uids=89824..., pp. 1, 2002.

Burczak, et al., "Polymeric materials for biomedical purposes obtained by radiation methods. V. hybrid artificial pancreas", Polim Med, vol. 24, No. 1-2, pp. 45-55, 1994, abs: http://www.ncbi.nlm.nih.gov/entrez/query.fcgi?cmd=retrieve&db=PubMed&list_uids=7915..., pp. 1, 2002.

Choe, et al., "An experimental study of embolic effect according to infusion rate and concentration of suspension in transarterial particulate embolization", Invest Radiol, vol. 32, No. 5, pp. 260-270, 1997, abs: http://www.ncbi.nlm.nih.gov/entrez/query.fcgi?cmd=retrieve&db=PubMed&list_uids=9140745&dopt+Abs..., pp. 1, 2002.

Colombo M, "Treatment of Hepatocellular Carcinoma", University of Milan, Inst Internal Med, Irccs Maggiore Res Unit Liver, Canc, Firc, Via Pace 9 1-20122 Milan, Italy, Source: Journal of Viral Hepatitis, 1997;4:125-130, Available Web Site: http://home.texoma.net/~moreland/stats/hcc-9.html.

Derdeyn, et al., "Collagen-coated acrylic microspheres for embolotherapy: in vivo and in vitro characteristics", American Journal of Neuroradiology, vol. 18, No. 4, pp. 647-653, 1997, abs: http://www.ncbi.nlm.nih.gov/entrez/query.fcgi?cmd=retrieve&db=PubMed&list_uids=9127025&dopt=Abs..., pp. 1, 2002.

Derdeyn, et al., "Polyvinyl alcohol particle size and suspension characteristics", *American Journal of Neuroradiology*, vol. 16, pp. 1335-1343, 1995.

DiLuccio et al., "Sustained-Release Oral Delivery of Theophylline by Use of Polyvinyl Alcohol and Polyvinyl Alcohol-Methyl Acrylate Polymers", *Journal of Pharmaceutical Sciences*, Jan. 1994, vol. 83, No. 1, pp. 104-106.

Gander, et al., "Effect of polymeric network structure on drug release from cross-linked poly(vinyl alcohol) micromatrices", Pharm Res, vol. 6, No. 7, pp. 578-584, 1989, abs: http://www.ncbi.nlm.nih.gov/entrez/query.fcgi?cmd=retrieve&db=PubMed&list_uids=25080..., pp. 1, 2002.

Germano, et al., "Histopathological follow-up study of 66 cerebral arteriovenous malformations after therapeutic embolization with polyvinyl alcohol", J Neurosurg, vol. 76, No. 4, pp. 607-614, 1992, abs: http://www.ncbi.nlm.nih.gov/entrez/query.fcgi?cmd=retrieve&db=PubMed&list_uids=15452..., pp. 1, 2002.

Geschwind et al., "Chemoembolization of Liver Tumor in a Rabbit Model: Assessment of Tumor Cell Death with Diffusion-Weighted MR Imaging and Histologic Analysis", *Journal of Vascular and Interventional Radiology*, Dec. 2000, vol. 11, No. 10, pp. 1244-1255.

Gohel, et al., "Formulation design and optimization of modified-release microspheres of diclofenac sodium", Drug Dev Ind Pharm, vol. 25, No. 2, pp. 247-251, 1999, abs: http://www.ncbi.nlm.nih.gov/entrez/query.fcgi?cmd=retrieve&db=PubMed&list_uids=10065360&dop=A..., pp. 1, 2002.

Goodwin, et al., "Overview of embolic agents and their indications", *Eleventh Annual International Symposium on Endovascular Therapy*, pp. 303-306, 1999.

Goodwin, et al., "Preliminary experience with uterine artery embolization for uterine fibroids", *Journal of Vascular and Interventional Radiology*, vol. 8, No. 4, pp. 517-526, 1997.

Grandfils, et al., "Preparation of poly (D,L) lactide microspheres by emulsion solvent evaporation, and their clinical implications as a convenient embolic material", J Biomed Mater Res, vol. 26, No. 4, pp. 467-479, 1992, abs: http://www.ncbi.nlm.nih.gov/entrez/query.fcgi?cmd=retrieve&db=PubMed&list_uids=1601900&dopt=Abs . . . , pp. 1, 2002.

Hamada, et al., "Embolization with cellulose porous beads, II: Clinical Trial", abs:http://www.ajnr.org/content/abstract/17/10/1901?ijkey=R.a2vRMietlXw, pp. 1-2, 2002.

Horak, et al., "Hydrogels in endovascular embolization II. Clinical use of spherical particles", *Biomaterials*, vol. 7, 1986.

Huang, et al., "Percutaneous endovascular embolization of intracerebral arteriovenous malformations. Experience in 72 cases", Chin Med J, vol. 108, No. 6, pp. 413-419, 1995, abs: http://www.ncbi.nlm.nih.gov/entrez/query.fcgi?cmd=retrieve&db=PubMed&list_uids=75552..., pp. 1, 2002.

International Search Report for International Application No. PCT/US01/06981 (2 pages), Jun. 21, 2001.

Jack, et al., "Radiolabeled polyvinyl alcohol particles: a potential agent to monitor embolization procedures", Int J Rad Appl Instrum B, vol. 13, No. 3, pp. 235-243, 1986, abs: http://www.ncbi.nlm.nih.gov/entrez/query.fcgi?cmd=retrieve&db=PubMed&list_uids=37712, pp. 1, 2002.

Jiaqi, Y. et al., "A New Embolic Material: Super Absorbent Polymer (SAP) Microsphere and Its Embolic Effects", *Nippon Acta Radiologica* 1996 (56):19-24.

Joy C, et al., 1991, "Use of Preoperative Embolization in the Treatment of Vascular Metastatic Lesions of the Spine" Available Web Site: http://www.aaos.org/wordhtml/anmeet91/scipro/ppr472.htm.

Kai, et al., "The utility of the microcrystalline cellulose sphere as a particulate embolic agent: an experimental study", American Journal of Radiology, vol. 21, No. 6, pp. 1160-1163, 2000, or http://www.ajnr.org/cgi/content/full/21/6/1160, pp. 1-7, 2002.

Kan, et al., "In vivo microscopy of the liver after injection of lipiodol into the hepatic artery and portal vein in the rat", *Acta Radiologica*, vol. 30, pp. 419-425, 1989.

Kerber et al., "Polyvinyl Alcohol Foam: Prepackaged Emboli for Therapeutic Embolization", *American Journal Roentgenol*, Jun. 1978, vol. 130, pp. 1193-1194.

Kerber, "Flow-Controlled Therapeutic Embolization: A Physiologic and Safe Technique", *AJR*, Mar. 1980, vol. 134, pp. 557-561.

Kim et al., "Hollow Silica Spheres of Controlled Size and Porosity by Sol-Gel Processing," J. Am. Ceram. Soc., 74(8):1987-1992 (Aug. 1991).

Kim, et al., "Composite poly(vinyl alcohol) beads for controlled drug delivery", Pharm Res, vol. 9. No. 1, pp. 10-16, 1992, abs: http://www.ncbi.nlm.nih.gov/entrez/query.fcgi?cmd=retrieve&db=PubMed&list_uids=1589392&dopt=Abs..., pp. 1, 2002.

Kurata, et al., "Preoperative embolization for meningiomas using PVA particles", No Shinkei Geka, vol. 20, No. 4, pp. 367-373, 1992, abs: http://www.ncbi.nlm.nih.gov/entrez/query.fcgi?cmd=retrieve&db=PubMed&list_uids=1570057&dopt=Abs..., pp. 1, 2002.

Kurosaki et al., "Evaluation of PVA-Gel Spheres as GI-Transit Time Controlling Oral Drug Delivery System", *Proceedings of the 19th International Symposium on Controlled Release of Bioactive Materials*, Jul. 26-31, 1992, Orlando, Florida, pp. 273-274.

Kusano, et al., "Low-dose particulate polyvinylalcohol embolization in massive small artery intenstinal hemorrahage. Experimental and clinical results", Invest Radiol, vol. 22, No. 5, pp. 388-392, 1987, abs: http://www.ncbi.nlm.nih.gov/entrez/query.fcgi?cmd=retrieve&db=PubMed&list_uids=34963..., pp. 1, 2002.

Labarre et al., "Complement activation by substituted polyacrylamide hydrogels for embolisation and implantation", *Biomaterials*, vol. 23, pp. 2319-2327, 2002.

Lammer, et al., "Transcatheteral embolization with polyvinyl alcohol—technic and experimental studies", Rontgenblatter, vol. 36, No. 1, pp. 10-14, 1983, abs: http://www.ncbi.nlm.nih.gov/entrez/query.fcgi?cmd=retrieve&db=PubMed&list_uids=6823530&dop=Abs..., pp. 1, 2002.

Latchaw et al., "Polyvinyl Foam Embolization of Vascular and Neoplastic Lesions of the Head, Neck, and Spine", *Radiology*, Jun. 1979, vol. 131, pp. 669-679.

Leung et al., "Determinants of Postembolization Syndrome after Hepatic Chemoembolization", *Journal of Vascular and Interventional Radiology*, Mar. 2001, vol. 12, No. 3, pp. 320-326.

Markoff, et al., "Uterine arteriovenous malformation successfully embolized with a liquid polymer, isobutyl 2-cyanoacrylate", pp. 659-660, 1999.

Markus, H.S., "Experimental Aspects of High-Intensity Transient Signals in the Detection of Emboli," *J Clin Ultrasound* 23:81-87 (1995).

Matsumaru, et al., "Embolic materials for endovascular treatment of cerebral lesions", J Biomater Sci Polym Ed, vol. 8, No. 7, pp. 555-569, 1997, abs: http://www.ncbi.nlm.nih.gov/entrez/query.fcgi?cmd=retrieve&db=PubMed&list_uids=91953..., pp. 1, 2002.

Mavligit, G. et al., "Gastrointestinal Leiomyosarcoma Metastatic to the Liver", *Cancer*, vol. 75, No. 8, Apr. 15, 1995, pp. 2083-2088.

Mid-America Interventional Radiological Society, "New Treatment for Uterine Fibroids Avoids Surgery", Available Web Site: http://www.mirs.org/fibroids.htm, Oct. 1999.

Nakabayashi, et al., "Evaluation of particulate embolic materials with MR imaging, scanning electron microscopy, and phase-contrast microscopy", American Journal of Neuroradiology, vol. 18, No. 3, pp. 485-491, 1997, abs: http://www.ncbi.nlm.nih.gov/entrez/query.fcgi?cmd=retrieve&db=PubMed&list_uids=909004..., pp. 1, 2002.

Nakstad, et al., "Embolization of intracranial arteriovenous malformations and fistulas with polyvinyl alcohol particles nad platinum fibre coils", Neuroradiology, vol. 34, No. 4, pp. 348-351, 1992, abs:

http://www.ncbi.nlm.nih.gov/entrez/query.fcgi?cmd=retrieve&db=PubMed&list_uids=15284..., pp. 1, 2002.

Nash, et al., "Modifications of polystyrenic matrices for the purification of proteins. II. Effect of the degree of glutaraldehyde-poly(vinyl alcohol) crosslinking on various dye ligand chromatography systems", J Chromatogr A, vol. 776, No. 1, pp. 55-63, 1997, abs: http://www.ncbi.nlm.nih.gov/entrez/query.fcgi?cmd=retrieve&db=PubMed&list_uids=92860..., pp. 1, 2002.

Nikishin LF et al., 1999, "Interventional radiology in diffuse toxic goiter", European Congress of Radiology—ECR 1999, Available Web Site: http://www.ecr.org/conferences/ecr1999/sciprg/abs/p090041.htm.

Ophir, et al., "Ultrasonic backscatter from contrast producing collagen microspheres", *Ultrasonic Imaging*, vol. 2, pp. 67-77, 1980.

Oregon Health Sciences University, "Fibroid Embolization", Available Web Site: http://www.uhmc.edu/dotter-fibroid, Feb. 23, 2009.

Parker, et al., "A particulate contrast agent with potential for ultrasound imaging of liver", *Ultrasound in Medicine and Biology*, vol. 13, No. 9, pp. 555-566, 1987.

Pesant A.C. et al., 1997, "Dural fistulas involving the cavernous sinus: Treatment by embolization—7 cases", European Congress of Radiology—ECR 199, Available Web Site: http://www.ecr.org/conferences/ecr1997/sciprg/abs/9703088p.htm.

Physicians' Desk Reference Family Guide to Women's Health, "Chapter 7—Common Disorders of the Reproductive System", Available Web Site: http://www.healthsquare.com/pdrfg/wh/chapters/whlch01.htm, Jan. 15, 1994.

Pritchard, et al., "*Poly(Vinyl Alcohol)*: *Basic Properties and Uses*", London, England: Gordon and Breach Science Publishers, 1970.

Purdy, et al., "Arteriovenous malformations of the brain: choosing embolic materials to enhance safety and ease of excision", J Neurosurg, vol. 77, No. 2, pp. 217-222, 1992, abs: http://www.ncbi.nlm.nih.gov/entrez/query.fcgi?cmd=retrieve&db=PubMed&list_uids=16250..., pp. 1, 2002.

Quisling, et al., "Histopathology analysis of intraarterial polyvinyl alcohol microemboli in rat cerebral cortex", *American Journal of Neuroradiology*, vol. 5, pp. 101-104, 1984.

Rajan et al., "Sarcomas Metastatic to the Liver: Response and Survival after Cisplatin, Doxorubicin, Mitomycin-C, Ethiodol, and Polyvinyl Alcohol Chemoembolization", *Journal of Vascular and Interventional Radiology*, Feb. 2001, vol. 12, No. 2, pp. 187-193.

Ramos, et al., "Tumor vascular signals in renal masses: detection with Doppler US", *Radiology*, vol. 168, No. 3, pp. 633-637, 1988.

Repa, I. et al., "Mortalities Associated with Use of a Commercial Suspension of Polyvinyl Alcohol", *Radiology* 1989; 170:395-399.

Rump, A. et al., "Pharmacokinetics of Intraarterial Mitomycin C in the Chemoembolisation Treatment of Liver Metastases", *Gen. Pharmac.* vol. 27, No. 4, pp. 669-671, 1996.

Schwarz, K.Q., "The Acoustic Filter: An Ultrasonic Blood Filter for the Heart-Lung Machine," *Journal of Thoracic and Cardiovascular Surgery* 104(6):1647-1653 (1992).

Shafik, A., "Intraesophageal Polytef injection for the treatment of reflux esophagitis", Department of Surgery and Experimental Research, Faculty of Medicine, Cairo University, Cairo, Egypt, pp. 1-2, Received: Jun. 22, 1994; Accepted: Oct. 15, 1994, http://www.ahmedshafik.org/Group-D/d016.htm.

Spickler, et al., "The MR appearance of endovascular embolic agents in vitro with clinical correlation", Comput Med Imaging Graph, vol. 14, No. 6, pp. 415-423, 1990, abs: http://www.ncbi.nlm.nih.gov/entrez/query.fcgi?cmd=retrieve&db=PubMed&list_uids=21487..., pp. 1, 2002.

Spies JB, "Georgetown University Medical Center. Uterine Fibroid Embolization (UFE). An alternative to surgery for patients with uterine fibroids. Literature Review.", Available Web Site: http://www.dml.georgetown.edu/fibroids, Feb. 4, 2004.

Stridbeck, H. et al., "Collateral Circulation Following Repeated Distal Embolization of the Hepatic Artery in Pigs," *Invest Radiol* 1984;19:179-183.

Strunk, et al., "Treatment of congenital coronary arteriovenous malformations with microparticle embolization", Cathet Cardiovasc Diagn, vol. 22, No. 2, pp. 133-136, 1991, abs: http://www.ncbi.nlm.nih.gov/entrez/query.fcgi?cmd=retrieve&db=PubMed&list_uids=2009563&dop=Abs..., pp. 1, 2002.

Swanson DA et al., 1980, "The role of embolization and nephrectomy in the treatment of metastatic renal carcinoma", Urologic Clinics of North America 7(3):719-730, 1980. University of Pennsylvania Cancer Center—Oncolink., Available Web Site: http://www.oncolink.upenn.edu/pdg_html/cites/00/00585.html.

Tabata et al., "Tumor accumulation of poly(vinyl alcohol) of different sizes after intravenous injection", *Journal of Controlled Release*, Jan. 2, 1998, vol. 50, Nos. 1-3, pp. 123-133.

Tadavarthy et al., "Polyvinyl Alcohol (Ivalon) as an Embolizing Agent", *Seminars in Interventional Radiology*, vol. 1, No. 2, Department of Radiology, University of Minnesota Hospitals, Minneapolis, Minnesota, Jun. 1984, pp. 101-109.

Tadavarthy et al., "Polyvinyl Alcohol (Ivalon) as an Embolizing Agent", *The American Journal of Roentgenology Radium Therapy and Nuclear Medicine*, Nov. 1975, vol. 125, No. 3, pp. 609-616.

Tao, et al., "Study of microspheres for embolization of the hepatic artery", Yao Xue Xue Bao, vol. 23, No. 1, pp. 55-60, 1988, abs: http://www.ncbi.nlm.nih.gov/entrez/query.fcgi?cmd=retrieve&db=PubMed&list_uids=3400477&dop=A, pp. 1, 2002.

Tao, et al., "Study on embolization of hepatitic artery using microspheres", Acta Pharmaceutica Sinica vol. 23, No. 1, pp. 55-60; 1988. Translation.

Terada, et al., "Preoperative embolization of meningiomas fed by ophthalmic branch arteries", Surg Neurol, vol. 45, No. 2, pp. 161-166, 1996, abs: http://www.ncbi.nlm.nih.gov/entrez/query.fcgi?cmd=retrieve&db=PubMed&list_uids=86070..., pp. 1, 2002.

Thanoo, B. C. et al., "Preparation and Properties of Barium Sulphate and Methyl Iothalamate Loaded Poly(vinyl Alcohol) Microspheres as Radiopaque Particulate Emboli", *Journal of Applied Biomaterials*, vol. 2, 67-72 (1991).

Thanoo, et al., "Controlled release of oral drugs from cross-linked polyvinyl alcohol microspheres", J Pharm Pharmacol, vol. 45, No. 1, pp. 16-20, 1993, abs: http://www.ncbi.nlm.nih.gov/entrez/query.fcgi?cmd=retrieve&db=PubMed&list_uids=8094438&dop=Abs..., pp. 1, 2002.

Thanoo, et al., "Tantalum loaded silicone micropsheres as particulate emboli", J Microencapsul, vol. 8, No. 1, pp. 95-101, 1991, abs: http://www.ncbi.nlm.nih.gov/entrez/query.fcgi?cmd=retrieve&db=PubMed&list_uids=1880697&dop=Abs..., pp. 1, 2002.

Tikkakoski, et al., "Preoperative embolization in the management of neck paragangliomas", *Laryngoscope*, vol. 107, pp. 821-826, 1997.

Touho, et al., "Intravascular treatment of spinal arteriovenous malformations using a microcatheter—with special reference to serial xylocaine tests and intravascular pressure monitoring", Surgical Neurology, vol. 42, No. 2, pp. 148-156. 1994, abs: http://www.ncbi.nlm.nih.gov/entrez/query.fcgi?cmd=retrieve&db=PubMed&list_uids=80912..., pp. 1, 2002.

University Medical Center SUNY Stony Brook, Department of Urology, "Variococele and its treatment.", Available Web Site: http://www.hsc.sunysb.edu/urology/male_inf...variocoele_and_its_treatment.html, Oct. 30, 2009.

Vivas S et al., "Arterioportal fistula and hemobilia in a patient with hepatic transplant", Gastroenterol Hepatol, Feb. 1998;21(2):88-9, Available Web Site: http://www.doyma.es/copiani/revistas/gastro/abstr/abs_p080.html.

Wakhloo, et al., "Extended preoperative polyvinyl alcohol microembolization of intracranial meningiomas: Assessment of two embolization techniques", *American Journal of Neuroradiology*, vol. 14, pp. 571-582, 1993.

Walsh RM et al., 1998, "Role of Angiography and Embolization for Acute Massive Upper Gastronintestinal Hemorrhage." Department of General Surgery and Radiology, Cleveland Clinic Foundation, Cleveland, Ohio., Available Web Site: http://www.ssat.com/98ddw/abstscorrt-47.html.

Wikholm G et al., 1996, "Embolization of Cerebral Arteriovenous Malformations: Part I—Technique, Morphology, and Complications", Departments of Neurology (CL) and Interventional Radiology (GW, PS), Sahlgrenska University Hospital, Goteborg, Sweden., Neurosurgery. Sep. 1996;39(3):448-57; discussion 457-9., Available Web Site: http://www.wwilkins.com/neurosurgery/0148-396X9-96inter.html.

Worthington-Kirsch RL, 1999, "Interventionalists offer management option for uterine fibroids." Diagnostic Imaging, pp. 47-49., Available Web Site: http://www.dimag.com/references/9903wortrefs.html.

Worthington-Kirsch, et al., "Uterine arterial embolization for the management of leiomyomas: Quality-of-life assessment and clinical response", *Radiology*, vol. 208, No. 3, 625-629, 1998.

Wright, K.C. et al., "Partial Splenic Embolization Using Polyvinyl Alcohol Foam, Dextran, Polystyrene, or Silicone," *Radiology 142*:351-354, Feb. 1982.

Yamada, et al., "Extended intraarterial cisplatin infusion for treatment of gynecological cancer after alteration of intrapelvic blood flow and implantation of a vascular access device", *International Radiology*, May-Jun. 1996.

Yusi et al., "Submuscosal Injection of Polyvinyl Alcohol in Artificially Created Vesico-Ureteral Reflux: A Preliminary Report," Asian J. Surg. 18(2): 122-127 (Apr. 1995).

Zou, Ying-hua, et al. "Experimental Canine Hapatic Artery Embolization with Polyvinyl Alcohol Microspheres" (Translation), *Zhong Hua Fang-She Xue ZaZhi*, Dec. 23, 1989 (6):330-332.

Zou, Ying-hua, et al. "Experimental Canine Hapatic Artery Embolization with Polyvinyl Alcohol Microspheres", *Zhong Hua Fang-She Xue ZaZhi*, Dec. 23, 1989 (6):330-332.

\* cited by examiner

EMBOLIZATION

CROSS-REFERENCE TO RELATED APPLICATIONS

This application is a divisional of, and claims priority under 35 U.S.C. §120 to, U.S. patent application Ser. No. 10/651,475, filed Aug. 29, 2003, now U.S. Pat. No. 8,012,454 which is a continuation-in-part of U.S. patent application Ser. No. 10/232,265, filed on Aug. 30, 2002, now U.S. Pat. No. 7,462,366, the entire contents of both of which are being hereby fully incorporated by reference.

TECHNICAL FIELD

This invention relates to embolization.

BACKGROUND

Therapeutic vascular occlusions (embolizations) are used to prevent or treat pathological conditions in situ. Compositions including embolic particles are used for occluding vessels in a variety of medical applications. Delivery of embolic particles through a catheter is dependent on size uniformity, density and compressibility of the embolic particles.

SUMMARY

In one aspect, the invention features a particle that includes a polymeric matrix and a ferromagnetic material distributed in the polymeric matrix. The particle has a diameter of from about ten microns to about 3,000 microns.

In another aspect, the invention features a method of manufacturing particles. The method includes forming a mixture containing a polymer, a gelling compound, and a ferromagnetic material, and treating the mixture to form a particle that includes the polymeric matrix and the ferromagnetic material in the polymeric matrix. The particles have a mean diameter of from about ten microns to about 3,000 microns.

In a further aspect, the invention features a method that includes administering to a subject a therapeutically effective amount of embolic particles. The particles include a polymeric matrix and a ferromagnetic material distributed in the polymeric matrix. The particles have a mean diameter of from about ten microns to about 3,000 microns.

In one aspect, the invention features a particle that includes a polymeric matrix and a radiopaque material distributed in the polymeric matrix. The particle has a diameter of from about ten microns to about 3,000 microns. The particle has an interior with a density of large pores and a surface region with a density of large pores, and the density of large pores of the interior is greater than the density of large pores of the surface region.

In another aspect, the invention features a method of manufacturing particles. The method includes forming a mixture containing a polymer, gelling compound, and a radiopaque material, and treating the mixture to form a particle comprising a polymeric matrix and radiopaque material in the polymeric matrix. The particles have a diameter of from about ten microns to about 3,000 microns. The particles have an interior with a density of large pores and a surface region with a density of large pores, and the density of large pores of the interior is greater than the density of large pores of the surface region.

In a further aspect, the invention features a method that includes administering to a subject a therapeutically effective amount of embolic particles. The particles include a polymeric matrix and a radiopaque material distributed in the polymeric matrix. The particles have a mean diameter of from about ten microns to about 3,000 microns. The particles have an interior with a density of large pores and a surface region with a density of large pores, and the density of large pores of the interior is greater than the density of large pores of the surface region.

In one aspect, the invention features a particle that includes a polymeric matrix and an MRI-visible material distributed in the polymeric matrix. The particle has a diameter of from about ten microns to about 3,000 microns. The particle has an interior with a density of large pores and a surface region with a density of large pores, and the density of large pores of the interior is greater than the density of large pores of the surface region.

In another aspect, the invention features a method of manufacturing particles. The method includes forming a mixture containing a polymer, gelling compound, and an MRI-visible material, and treating the mixture to form a particle comprising a polymeric matrix and the MRI-visible material in the polymeric matrix. The particles have a mean diameter of from about ten microns to about 3,000 microns. The particles have an interior with a density of large pores and a surface region with a density of large pores, and the density of large pores of the interior is greater than the density of large pores of the surface region.

In a further aspect, the invention features a method that includes administering to a subject a therapeutically effective amount of embolic particles. The particles include a polymeric matrix and an MRI-visible material distributed in the polymeric matrix. The particles have a mean diameter of from about ten microns to about 3,000 microns. The particles have an interior with a density of large pores and a surface region with a density of large pores, and the density of large pores of the interior is greater than the density of large pores of the surface region.

In another aspect, the invention features a method that includes heating a plurality of particles disposed in a body lumen. The particles include a polymeric matrix and a ferromagnetic material distributed in the polymeric matrix. The particles have a diameter of from about ten microns to about 3,000 microns.

Embodiments can include one or more of the following.

A ferromagnetic material can be, for example, a metal (e.g., a transition metal), a metal alloy, a metal oxide, a soft ferrite, a rare-earth magnet alloy, or an amorphous and non-earth alloy. Examples of ferromagnetic materials include magnetite, nickel, cobalt, iron and Mu-metal.

A radiopaque material can be, for example, a metal, a metal alloy, a metal oxide, or a contrast agent. Examples of radiopaque materials include titanium dioxide, bismuth subcarbonate, platinum and barium sulfate.

An MRI-visible material can be, for example, a non-ferrous metal-alloy containing paramagnetic elements, a non-ferrous metallic band coated with an oxide or a carbide layer of dysprosium or gadolinium, a non-ferrous metal coated with a layer of superparamagnetic material, or a nanocrystalline particle of a transition metal oxide. Examples of MRI-visible materials include terbium-dysprosium, dysprosium, gadolinium, $Dy_2O_3$, and gadolinium-containing compounds (e.g., $Gd_2O_3$).

The material (ferromagnetic material, radiopaque material, MRI-visible material) can be in the shape of a particle.

The material (ferromagnetic material, radiopaque material, MRI-visible material) can have a diameter of from about two microns to about 20 microns (e.g., from about ten microns to about 12 microns).

The material (ferromagnetic material, radiopaque material, MRI-visible material) can be substantially homogeneously distributed in the polymeric matrix.

A particle containing a polymer matrix and a material (ferromagnetic material, radiopaque material, MRI-visible material) can have a diameter of at least about 100 microns (e.g., at least about 500 microns, at least about 1,000 microns, at least about 1,500 microns, at least about 2,000 microns, at most about 2,500 microns) and/or at most about 2,000 microns (e.g., at most about 1,500 microns, at most about 1,200 microns, at most about 1,000 microns, at most about 500 microns). For example, such a particle can have a diameter of from about 100 microns to about 500 microns, or from about 500 microns to about 1,200 microns.

A particle containing a polymer matrix and a material (ferromagnetic material, radiopaque material, MRI-visible material) can also include a therapeutic agent (e.g., in the particle and/or on the particle).

A particle containing a polymer matrix and a material (ferromagnetic material, radiopaque material, MRI-visible material) can be substantially spherical.

The polymeric matrix can include a polysaccharide (e.g., alginate).

The polymeric matrix can be formed of one or more polyvinyl alcohols, polyacrylic acids, polymethacrylic acids, poly vinyl sulfonates, carboxymethyl celluloses, hydroxyethyl celluloses, substituted celluloses, polyacrylamides, polyethylene glycols, polyamides, polyureas, polyurethanes, polyesters, polyethers, polystyrenes, polysaccharides, polylactic acids, polyethylenes, polymethylmethacrylates, polycaprolactones, polyglycolic acids, and/or poly(lactic-co-glycolic) acids.

A particle containing a polymer matrix and a material (ferromagnetic material, radiopaque material, MRI-visible material) can include two or more polymers. For example, one of the polymers can form a coating over another (e.g., matrix) polymer. The polymer coating can contain one or more ferromagnetic materials, one or more MRI-visible materials and/or one or more radiopaque materials. The density of the material(s) in the coating can be less than, greater than, or about the same as the density of the material(s) in the matrix polymer. The polymer coating can be bioabsorbable (e.g., formed of a polysaccharide such as alginate).

In some embodiments, a particle containing a polymeric matrix and a ferromagnetic material can contain pores. In certain embodiments, a particle containing a polymeric matrix and a ferromagnetic material can be nonporous.

In some embodiments in which a particle that contains a polymeric matrix and a ferromagnetic material contains pores, the density of large pores in an interior region of the particle can be greater than the density of large pores of the surface region.

A particle containing a polymer matrix and a material (ferromagnetic material, radiopaque material, MRI-visible material) can contain from about 0.1 percent to about 90 percent by weight (e.g., from about 0.1 percent to about 75 percent by weight) of the ferromagnetic material, MRI-visible material or radiopaque material.

A particle containing a polymer matrix and a material (ferromagnetic material, radiopaque material, MRI-visible material) can have a coating that includes an inorganic, ionic salt.

The gelling compound used in a method to make a particle can be a polysaccharide (e.g. alginate).

A method of making a particle can include forming drops of the mixture that contains the polymer and gelling agent. The method can include contacting the drops with a gelling agent. The method can further include reacting the polymer. The method can also include removing the gelling compound. The method can include combining the particles with a pharmaceutically acceptable medium.

A method of administering embolic particles can include administration by percutaneous injection.

A method of administering embolic particles can include administration by a catheter.

A method of administering embolic particles can include applying a magnetic field to direct the particles. The magnetic field can be external to a subject, internal to the subject, or both. The particles can be directed with a catheter comprising a magnet.

A method of administering embolic particles can include releasing the therapeutic agent from the particles.

A method can include ablating body tissue.

In some embodiments, heating the particles can include exposing the particles to RF radiation.

In some embodiments, heating the particles heats body tissue.

Embodiments of the invention may have one or more of the following advantages.

In some embodiments, a particle can contain one or more components that are biocompatible. As an example, a particle can include one or more biocompatible polymers (e.g., one or more bioabsorable polymers). As another example, a particle can contain one or more materials (e.g., one or more radiopaque materials, one or more ferromagnetic materials, one or more MRI-visible materials) that are biocompatible. In certain embodiments, a particle can include one or more biocompatible polymers (e.g., one or more bioabsorable polymers) and one or more additional biocompatible materials (e.g., one or more radiopaque materials, one or more ferromagnetic materials, one or more MRI-visible materials).

In embodiments in which a particle contains one or more radiopaque materials, the particle can exhibit enhanced visibility under X-ray fluoroscopy (e.g., when the particle is in a subject). In certain embodiments, the presence of one or more radiopaque materials can allow the particle to be viewed using X-ray fluoroscopy in the absence of a radiopaque contrast agent. This can allow a physician or technician to view the particle in an embolic composition (e.g., prior to delivering the particles from a catheter) via a non-invasive technique, allow the physician or technician to position the particles at a desired location within the subject (e.g., by positioning the delivery portion of the catheter at a desired location within the subject and then delivering the embolic composition into the subject), and/or allow the physician or technician to monitor the progress of a procedure and/or determine whether the particles are migrating to a site that is not targeted for treatment.

In embodiments in which a particle contains one or more MRI-visible materials, the particle can exhibit enhanced visibility under MRI (e.g., when the particle is in a subject). In certain embodiments, the presence of one or more MRI-visible materials can allow the particle to be viewed using MRI in the absence of an MRI contrast agent. This can allow a physician or technician to view the particle in an embolic composition (e.g., prior to delivering the particles from a catheter) via a non-invasive technique, allow the physician or technician to position the particles at a desired location within the subject (e.g., by positioning the delivery portion of the catheter at a desired location within the subject and then delivering the embolic composition into the subject), and/or allow the physician or technician to monitor the progress of a procedure and/or determine whether the particles are migrating to a site that is not targeted for treatment.

In embodiments in which a particle contains one or more ferromagnetic materials, the positioning of the particle can be relatively easily and/or non-invasively controlled using a magnetic field (e.g., a magnetic field outside a subject, a magnetic field inside a subject, or both). As an example, the particle can be steered through a body lumen (e.g., to a relatively distal location of a lumen that might otherwise be difficult for the particle to reach) by applying a magnetic field to the particle. As another example, the ability of the particle to migrate from a desired location can be reduced by applying a magnetic field.

In some embodiments (e.g., when a particle contains a ferromagnetic material), the particle can enhance RF ablation procedures.

Features and advantages are in the description, drawings, and claims.

DETAILED DESCRIPTION

Figure 1:
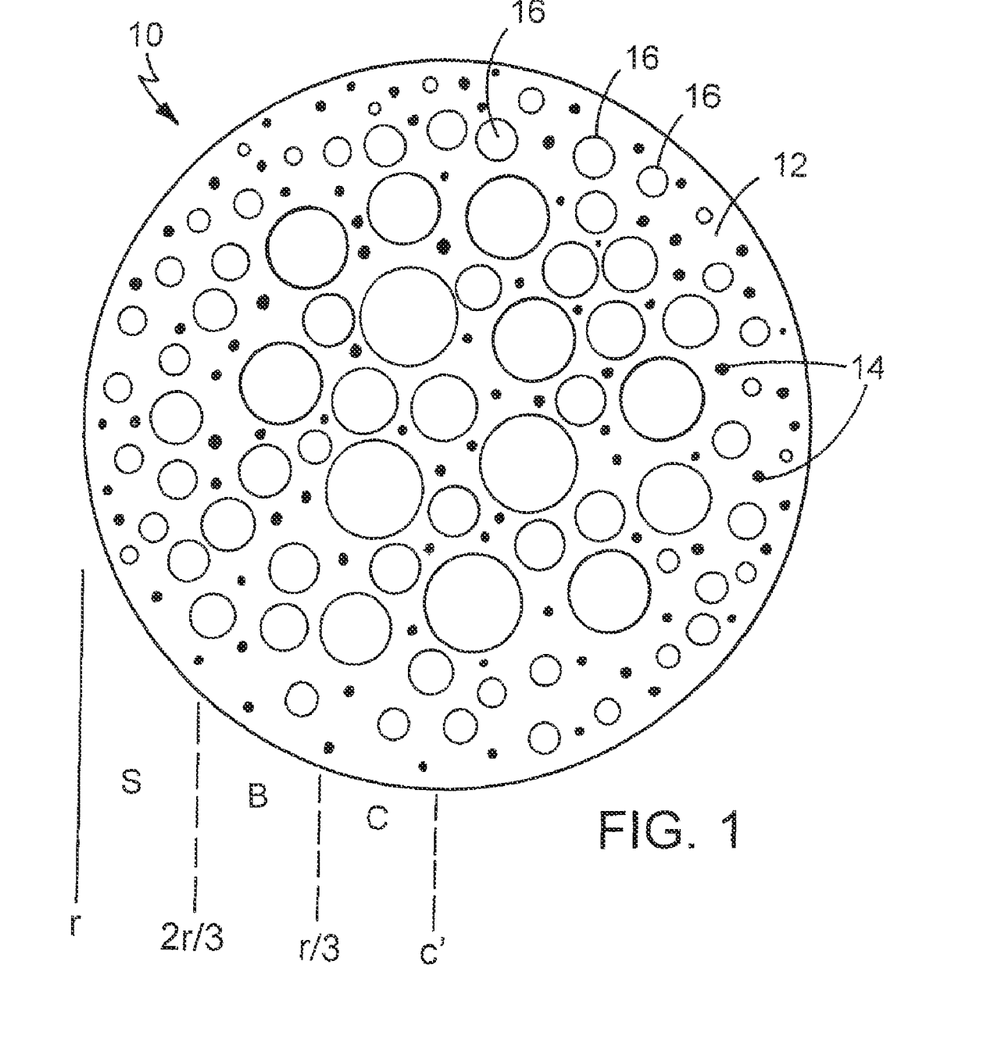
FIG. 1 is a cross-sectional view of an embodiment of a particle.

Referring to FIG. 1, a substantially spherical particle 10 includes a matrix 12, a material 14 and pores 16. Material 14, which is formed of one or more radiopaque materials, one or more MRI-visible materials, and/or one or more ferromagnetic materials, is substantially homogeneously distributed in matrix 12. Pores 16 are regions of particle 10 that are substantially devoid of matrix 12 and material 14. In some embodiments, pores 16 contain a gas, such as air.

In general, particle 10 has a diameter of about 3,000 microns or less (e.g., about 2,500 microns or less; about 2,000 microns or less; about 1,500 microns or less; about 1,200 microns or less; about 1,000 microns or less; about 900 microns or less; about 700 microns or less; about 500 microns or less; about 400 microns or less; about 300 microns or less; about 100 microns or less) and/or about ten microns or more (e.g., about 100 microns or more; about 300 microns or more; about 400 microns or more; about 500 microns or more; about 700 microns or more; about 900 microns or more; about 1,000 microns or more; about 1,200 microns or more; about 1,500 microns or more; about 2,000 microns or more; about 2,500 microns or more). In certain embodiments, the diameter of particle 10 can be from about 100 microns to about 700 microns; from about 500 microns to about 700 microns; from about 100 microns to about 500 microns; from about 100 microns to about 300 microns; from about 300 microns to about 500 microns; from about 500 microns to about 1,200 microns; from about 500 microns to about 700 microns; from about 700 microns to about 900 microns; from about 900 microns to about 1,200 microns.

As shown in FIG. 1, particle 10 can be considered to include a center region, C, from the center c' of particle 10 to a radius of about r/3, a body region, B, from about r/3 to about 2 r/3, and a surface region, S, from about 2r/3 to r. The regions can be characterized by the relative size of pores 16 present in particle 10 in each region, the density of pores 16 (the number of pores 16 per unit volume of particle 10) in each region, and/or the mass density (the density of the matrix 12 and material 14 mass per unit volume of particle 10) in each region.

In general, the mean size of pores 16 in region C of particle 10 is greater than the mean size of pores 16 at region S of particle 10. In some embodiments, the mean size of pores 16 in region C of particle 10 is greater than the mean size of pores 16 in region B particle 10, and/or the mean size of pores 16 in region B of particle 10 is greater than the mean size of pores 16 at region S particle 10. In some embodiments, the mean size of pores 16 in region C is about 20 microns or more (e.g., about 30 microns or more, from about 20 microns to about 35 microns). In certain embodiments, the mean size of pores 16 in region B is about 18 microns or less (e.g. about 15 microns or less, from about 18 microns to about two microns). In some embodiments, the mean size of pores 16 in region S is about one micron or less (e.g. from about 0.1 micron to about 0.01 micron). In certain embodiments, the mean size of pores 16 in region B is from about 50 percent to about 70 percent of the mean size of pores 16 in region C, and/or the mean size of pores 16 at region S is about ten percent or less (e.g., about two percent or less) of the mean size of pores 16 in region B. In some embodiments, the surface of particle 10 and/or its region S is/are substantially free of pores having a diameter greater than about one micron (e.g., greater than about ten microns). In certain embodiments, the mean size of pores 16 in the region from 0.8r to r (e.g., from 0.9r to r) is about one micron or less (e.g., about 0.5 micron or less, about 0.1 micron or less). In some embodiments, pores 16 in the region from the center of particle 10 to 0.9r (e.g., from the center of particle 10 to 0.8r) are about ten microns or greater and/or have a mean size of from about two microns to about 35 microns. In certain embodiments, the mean size of pores 16 in the region from 0.8r to r (e.g., from 0.9r to r) is about five percent or less (e.g., about one percent or less, about 0.3 percent or less) of the mean size of pores 16 in the region from the center to 0.9r. In some embodiments, the largest pores in particle 10 can have a size in the range of about one percent or more (e.g., about five percent or more, about ten percent or more) of the diameter of particle 10. The size of pores 16 in particle 10 can be measured by viewing a cross-section of particle 10. For irregularly shaped (nonspherical) pores, the maximum visible cross-section is used.

Generally, the density of pores 16 in region C of particle 10 is greater than the density of pores 16 at region S of particle 10. In some embodiments, the density of pores 16 in region C of particle 10 is greater than the density of pores 16 in region B of particle 10, and/or the density of pores 16 in region B of particle 10 is greater than the density of pores 16 at region S of particle 10.

In general, the mass density in region C of particle 10 is less than the mass density at region S of particle 10. In some embodiments, the mass density in region C of particle 10 is less than the mass density in region B of particle 10, and/or the mass density in region B of particle 10 is less than the mass density at region S of particle 10.

In general, the density of particle 10 (e.g., as measured in grams of material per unit volume) is such that it can be readily suspended in a carrier fluid (e.g., a pharmaceutically acceptable carrier, such as a saline solution, a contrast solution, or a mixture thereof) and remain suspended during delivery. In some embodiments, the density of particle 10 is from about 1.1 grams per cubic centimeter to about 1.4 grams per cubic centimeter. As an example, for suspension in a saline-contrast solution, the density of particle 10 can be from about 1.2 grams per cubic centimeter to about 1.3 grams per cubic centimeter.

In certain embodiments the region of small pores near the surface of particle 10 can be relatively stiff and incompressible, which can enhance resistance to shear forces and abrasion. In addition, the variable pore size profile can produce a symmetric compressibility and, it is believed, a compressibility profile. As a result, particle 10 can be relatively easily compressed from a maximum, at rest diameter to a smaller, compressed first diameter. Compression to an even smaller diameter, however, may involve substantially greater force. Without wishing to be bound by theory, it is believed that a variable compressibility profile can be the result of a relatively weak, collapsible inter-pore wall structure in the center region of particle 10 (where the pores are relatively large), and a stiffer inter-pore wall structure near the surface of particle 10 (where the pores are more numerous and relatively small). It is further believed that a variable pore size profile can enhance elastic recovery after compression. It is also believed that the pore structure can influence the density of particle 10 and the rate of carrier fluid or body fluid uptake.

In some embodiments, a plurality of the particles (e.g., in an embolic composition) can be delivered through a catheter having a lumen with a cross-sectional area that is smaller (e.g., about 50 percent or less) than the uncompressed cross-sectional area of the particles. In such embodiments, the particles are compressed to pass through the catheter for delivery into the body. Typically, the compression force is provided indirectly, by depressing the syringe plunger to increase the pressure applied to the carrier fluid. In general, the particles are relatively easily compressed to diameters sufficient for delivery through the catheter into the body. The relatively robust, rigid surface region of the particles can resist abrasion when the particles contact hard surfaces such as syringe surfaces, hard plastic or metal stopcock surfaces, and/or the catheter lumen wall (made of, e.g., Teflon) during delivery. Once in the body, the particles can substantially recover to original diameter and shape for efficient transport in the carrier and body fluid stream. At the point of occlusion, the particles can again compress as they aggregate in the occlusion region. The particles can form a relatively dense occluding mass. The compression of the particles in the body is generally determined by the force provided by body fluid flow in the lumen. In some embodiments, the compression may be limited by the compression profile of the particles, and the number of particles needed to occlude a given diameter may be reduced.

In certain embodiments, the sphericity of particle 10 after compression in a catheter (e.g., after compression to about 50 percent or more of the cross-sectional area of particle 10) is about 0.8 or more (e.g., about 0.85 or more, about 0.9 or more, about 0.95 or more, about 0.97 or more). Particle 10 can be, for example, manually compressed, essentially flattened, while wet to about 50 percent or less of its original diameter and then, upon exposure to fluid, regain a sphericity of about 0.8 or more (e.g., about 0.85 or more, about 0.9 or more, about 0.95 or more, about 0.97 or more). As referred to herein, the sphericity of a particle is calculated using the equations in Appendix A. The relevant parameters of a particle can be determined using a Beckman Coulter RapidVUE Image Analyzer version 2.06 (Beckman Coulter, Miami, Fla.).

Porous particles are described, for example, in U.S. patent application Ser. No. 10/637,130, filed on Aug. 8, 2003, and entitled "Embolization", which is incorporated herein by reference.

In general, matrix 12 is formed of one or more polymers. Examples of polymers include polyvinyl alcohols, polyacrylic acids, polymethacrylic acids, poly vinyl sulfonates, carboxymethyl celluloses, hydroxyethyl celluloses, substituted celluloses, polyacrylamides, polyethylene glycols, polyamides, polyureas, polyurethanes, polyesters, polyethers, polystyrenes, polysaccharides, polylactic acids, polyethylenes, polymethylmethacrylates, polycaprolactones, polyglycolic acids, poly(lactic-co-glycolic) acids (e.g., poly (d-lactic-co-glycolic) acids), and copolymers or mixtures thereof. In some embodiments, matrix 12 can be substantially formed of a highly water insoluble, high molecular weight polymer. An example of such a polymer is a high molecular weight polyvinyl alcohol (PVA) that has been acetalized. Matrix 12 can be substantially pure intrachain 1,3-acetalized PVA and substantially free of animal derived residue such as collagen. In some embodiments, particle 10 includes a minor amount (e.g., about 2.5 weight percent or less, about one weight percent or less, about 0.2 weight percent or less) of a gelling material (e.g., a polysaccharide, such as alginate). In certain embodiments, the majority (e.g., at least about 75 weight percent, at least about 90 weight percent, at least about 95 weight percent) of matrix 12 is formed of a bioabsorbable polymer (e.g., polysaccharide, such as alginate).

In general, the amount of matrix 12 contained in particle 10 can be varied as desired. In some embodiments, particle 10 can include about 99.9 percent by weight or less (e.g., about 99.5 percent by weight or less, about 99 percent by weight or less, about 95 percent by weight or less, about 90 percent by weight or less, about 80 percent by weight or less, about 70 percent by weight or less, about 60 percent by weight or less, about 50 percent by weight or less, about 40 percent by weight or less, about 30 percent by weight or less, about 20 percent by weight or less) and/or about ten percent by weight or more (e.g., about 20 percent by weight or more, about 30 percent by weight or more, about 40 percent by weight or more, about 50 percent by weight or more, about 60 percent by weight or more, about 70 percent by weight or more, about 80 percent by weight or more, about 90 percent by weight or more, about 95 percent by weight or more) of matrix 12.

In some embodiments, material 14 is formed of one or more ferromagnetic materials. As used herein, a ferromagnetic material refers to a material that has a magnetic susceptibility of at least about 0.075 or more (e.g., at least about 0.1 or more; at least about 0.2 or more; at least about 0.3 or more; at least about 0.4 or more; at least about 0.5 or more; at least about one or more; at least about ten or more; at least about 100 or more; at least about 1,000 or more; at least about 10,000 or more) when measured at 25° C. A ferromagnetic material can be, for example, a metal (e.g., a transition metal such as nickel, cobalt, or iron), a metal alloy (e.g., a nickel-iron alloy such as Mu-metal), a metal oxide (e.g., an iron oxide such as magnetite), a ceramic nanomaterial, a soft ferrite (e.g., nickel-zinc-iron), a magnet alloy (e.g., a rare earth magnet alloy such as a neodymium-iron-boron alloy or a samarium-cobalt alloy), an amorphous alloy (e.g., iron-silicon-boron), a non-earth alloy, or a silicon alloy (e.g., an iron-zirconium-copper-boron-silicon alloy, an iron-zirconium-copper-boron-silicon alloy). Magnetite is commercially available from FerroTec Corporation (Nashua, N.H.), under the tradename EMG 1111 Ferrofluid. Iron-copper-niobium-boron-silicon alloys are commercially available from Hitachi Metals of America under the tradename Finemet™. Iron-zirconium-copper-boron-silicon alloys are commercially available from MAGNETEC GmbH under the tradename Nanoperm®.

In embodiments in which material 14 is a ferromagnetic material, a magnetic source can be used to move or direct the particles to a treatment site (see discussion below). The magnetic source can be external to the subject's body, or can be used internally. In some cases, both an external magnetic source and an internal magnetic source can be used to move the particles. An example of an internal magnetic source is a magnetic catheter. Magnetic catheters are described in U.S. patent application Ser. No. 10/108,874, filed on Mar. 29, 2002, and entitled "Magnetically Enhanced Injection Catheter", which is incorporated herein by reference. An example of an external magnetic source is a magnetic wand.

In some embodiments in which material 14 is a ferromagnetic material, the particles can be used to enhance the effects of an ablation procedure (e.g., an RF ablation procedure). For example, the particles can be used to enhance the ablation of a tumor. First, an RF probe (e.g., a 3.5 centimeter coaxial LeVeen electrode, available from RadioTherapeutics, Mountain View, Calif.) having tines at one end can be inserted into the area of the tumor. The particles can then be delivered to the area around the tines of the RF probe by, e.g., a catheter or a syringe. Thereafter, the tines can be deployed and the RF probe can be activated so that RF energy flows through the tines, thereby heating the tissue around the tines. Eventually, the tumor tissue can die as a result of the heating. Because they include ferromagnetic material, which can be relatively conductive, the particles can enhance the effects of ablation. For example, the circuit can be maintained for a longer period of time, resulting, e.g., in an increase in the area of the ablated surface. The end of the ablation period can be defined, for example, by the temperature of the ablated tissue or by the measured impedance of the circuit.

In certain embodiments in which material 14 is a ferromagnetic material, a magnetic field can be applied to the particles to affect the extent of conductivity. The magnetic field can be varied to adjust the conductivity of the particles (and, therefore, to adjust the extent of heating and ablation).

In some embodiments in which material 14 is a ferromagnetic material, the particles can be used in an agitation ablation process. In such a process, a magnetic field can be used to agitate the particles, such that the particles heat and/or physically deform the surrounding tissue, thereby ablating the surrounding tissue.

In some embodiments, material 14 is formed of one or more radiopaque materials. As used herein, a radiopaque material refers to a material having a density of about ten grams per cubic centimeter or greater (e.g., about 25 grams per cubic centimeter or greater, about 50 grams per cubic centimeter or greater). A radiopaque material can be, for example, a metal (e.g., tungsten, tantalum, platinum, palladium, lead, gold, titanium, silver), a metal alloy (e.g., stainless steel, an alloy of tungsten, an alloy of tantalum, an alloy of platinum, an alloy of palladium, an alloy of lead, an alloy of gold, an alloy of titanium, an alloy of silver), a metal oxide (e.g., titanium dioxide, zirconium oxide, aluminum oxide), bismuth subcarbonate, or barium sulfate. In some embodiments, a radiopaque material is a radiopaque contrast agent. Examples of radiopaque contrast agents include Omnipaque™, Renocal®, iodiamide meglumine, diatrizoate meglumine, ipodate calcium, ipodate sodium, iodamide sodium, iothalamate sodium, iopamidol, and metrizamide. Radiopaque contrast agents are commercially available from, for example, Bracco Diagnostic.

In embodiments in which material 14 is formed of one or more radiopaque materials, particle 10 can exhibit enhanced visibility under X-ray fluoroscopy, such as when particle 10 is in a subject (see discussion below). In some embodiments, X-ray fluoroscopy can be performed without the use of a radiopaque contrast agent.

In some embodiments, material 14 can include one or more MRI-visible materials. As used herein, a MRI-visible material refers to a material that has a magnetic susceptibility of at most about one or less (e.g., at most about 0.5 or less; at most about zero or less) when measured at 25° C. An MRI-visible material can be, for example, a non-ferrous metal-alloy containing paramagnetic elements (e.g., dysprosium or gadolinium) such as terbium-dysprosium, dysprosium, and gadolinium; a non-ferrous metallic band coated with an oxide or a carbide layer of dysprosium or gadolinium (e.g., $Dy_2O_3$ or $Gd_2O_3$); a non-ferrous metal (e.g., copper, silver, platinum, or gold) coated with a layer of superparamagnetic material, such as nanocrystalline $Fe_3O_4$, $CoFe_2O_4$, $MnFe_2O_4$, or $MgFe_2O_4$; or nanocrystalline particles of the transition metal oxides (e.g., oxides of Fe, Co, Ni). In some embodiments in which material 14 is formed of a ferromagnetic material, material 14 can also serve as an MRI-visible material if material 14 is present in a sufficiently low concentration. In some embodiments, an MRI-visible material can be an MRI contrast agent. Examples of MRI contrast agents include superparamagnetic iron oxides (e.g., ferumoxides, ferucarbotran, ferumoxsil, ferumoxtran (e.g., ferumoxtran-10), PEG-feron, ferucarbotran); gadopentetate dimeglumine; gadoterate meglumine; gadodiamide; gadoteridol; gadoversetamide; gadobutrol; gadobenate dimeglumine; mangafodipir trisodium; gadoxetic acid; gadobenate dimeglumine; macromolecular Gd-DOTA derivate; gadobenate dimeglumine; gadopentetate dimeglumine; ferric ammonium citrate; manganese chloride; manganese-loaded zeolite; ferristene; perfluoro-octylbromide; and barium sulfate. MRI contrast agents are described, for example, in U.S. patent application Ser. No. 10/390,202, filed on Mar. 17, 2003, and entitled "Medical Devices", which is incorporated herein by reference.

In embodiments in which material 14 is formed of one or more MRI-visible materials, particle 10 can exhibit enhanced visibility using MRI, such as when particle 10 is in a subject (see discussion below). In some embodiments, MRI can be performed without the use of an MRI contrast agent.

In certain embodiments, material 14 can be biocompatible. As an example, material 14 can be a biocompatible ferromagnetic material (e.g., magnetite). As another example, material 14 can be a biocompatible radiopaque material (e.g., magnetite). As an additional example, material 14 can be a biocompatible MRI-visible material (e.g., magnetite, gadolinium).

In some embodiments, material 14 can be bioerodable, such that material 14 can eventually break down in the body and either be dispersed throughout the body or excreted from the body. For example, material 14 can be a bioerodable ferromagnetic material. In such cases, material 14 may interfere with MRI-visibility when used in the body in a high concentration and/or a condensed form (e.g., when used in a particle). However, as material 14 is bioeroded and dispersed throughout the body or excreted from the body, its interference with MRI-visibility can decrease. Thus, a bioerodable ferromagnetic material 14 can be used, for example, for short-term embolic applications, without permanently interfering with MRI-visibility.

In some embodiments, both material 14 and matrix 12 can be biocompatible. For example, matrix 12 can be a polysaccharide (e.g., alginate), while material 14 is a biocompatible material (e.g., magnetite).

Generally, the amount of material 14 contained within particle 10 can be varied as desired. In some embodiments, particle 10 can include more than about 0.1 percent by weight (e.g., more than about 0.5 percent by weight, more than about one percent by weight, more than about five percent by weight, more than about ten percent by weight, more than about 20 percent by weight, more than about 30 percent by weight, more than about 40 percent by weight, more than about 50 percent by weight, more than about 60 percent by weight, more than about 70 percent by weight, more than about 80 percent by weight) and/or less than about 90 percent by weight (e.g., less than about 80 percent by weight, less than about 70 percent by weight, less than about 60 percent by weight, less than about 50 percent by weight, less than about 40 percent by weight, less than about 30 percent by weight, less than about 20 percent by weight, less than about ten percent by weight, less than about five percent by weight, less than about one percent by weight, less than about 0.5 percent by weight) of material 14.

In certain embodiments in which material 14 includes one or more ferromagnetic materials, particle 10 can include from about 0.1 percent by weight to about 90 percent by weight (e.g., from about 0.1 percent by weight to about 75 percent by weight, from about 0.1 percent by weight to about 50 percent by weight, from about one percent by weight to about 25 percent by weight) of the ferromagnetic material(s).

In some embodiments in which material 14 includes one or more radiopaque materials, particle 10 can include from about 0.1 percent by weight to about 50 percent by weight (e.g., from about 0.1 percent by weight to about 20 percent by weight, from about one percent by weight to about 20 percent by weight) of the radiopaque material(s).

In certain embodiments in which material 14 includes one or more MRI-visible materials, particle 10 can include from about five percent by weight to about 50 percent by weight (e.g., from about ten percent by weight to about 30 percent by weight) of the MRI-visible material(s).

In general, material 14 can be in any desired form (e.g., a solid, a liquid) and any desired shape (e.g., one or more particles, one or more fibers, one or more flakes, and/or one or more powders). In some embodiments, material 14 (e.g., a particle of material 14, a fiber of material 14, a flake of material 14, a powder of material 14) can have a width or diameter, and/or length, of less than about 40 microns (e.g., less than about 35 microns, less than about 30 microns, less than about 25 microns, less than about 20 microns, less than about 15 microns, less than about ten microns, less than about five microns, less than about one micron, less than about 0.5 micron, less than about 0.1 micron, less than about 0.05 micron, less than about 0.03 micron, less than about 0.01 micron) and/or more than about 0.005 micron (e.g., more than about 0.01 micron, more than about 0.03 micron, more than about 0.05 micron, more than about 0.1 micron, more than about 0.5 micron, more than about one micron, more than about five microns, more than about ten microns, more than about 15 microns, more than about 20 microns, more than about 25 microns, more than about 30 microns, more than about 35 microns). In some embodiments, material 14 (e.g., a particle of material 14, a fiber of material 14, a flake of material 14, a powder of material 14) can have a width or diameter, and/or a length, of from about two microns to about 20 microns (e.g., from about ten microns to about 12 microns).

As used herein, a fiber of material 14 has a ratio of its largest linear dimension to its smallest linear dimension of at least about 2:1 (e.g., at least about 3:1, at least about 5:1, at least about 10:1, at least about 15:1). In some embodiments, a fiber of material 14 has a ratio of its largest linear dimension to its smallest linear dimension of at most about 20:1 (e.g., at most about 15:1, at most about 10:1, about most about 5:1, at most about 3:1). In some embodiments, material 14 includes a mixture of fibers having two or more different aspect ratios.

In general, various methods can be used to prepare particle 10. In some embodiments, particle 10 is formed using a drop generator.

Figure 2A:
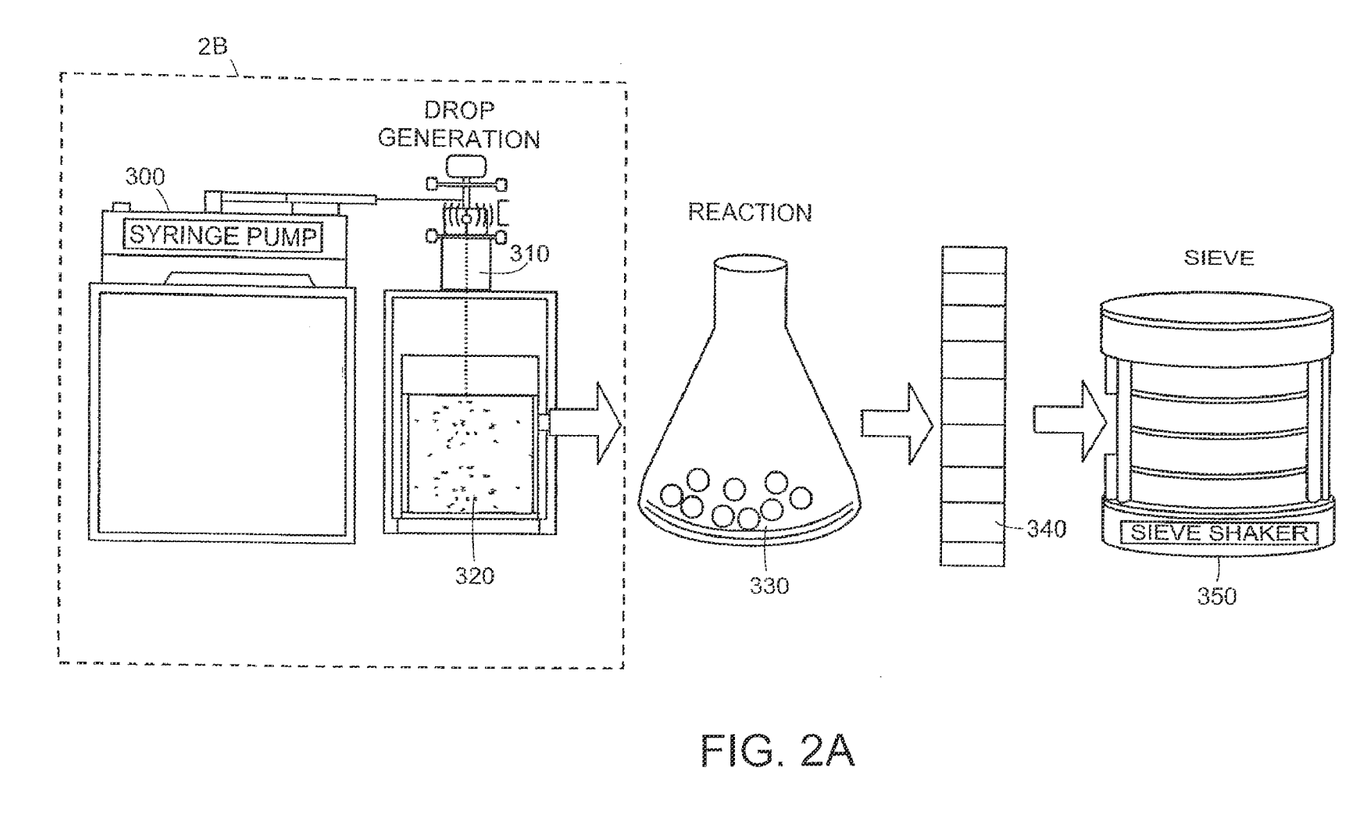
FIG. 2A is a schematic of an embodiment of a system for manufacturing particles.
Figure 2B:
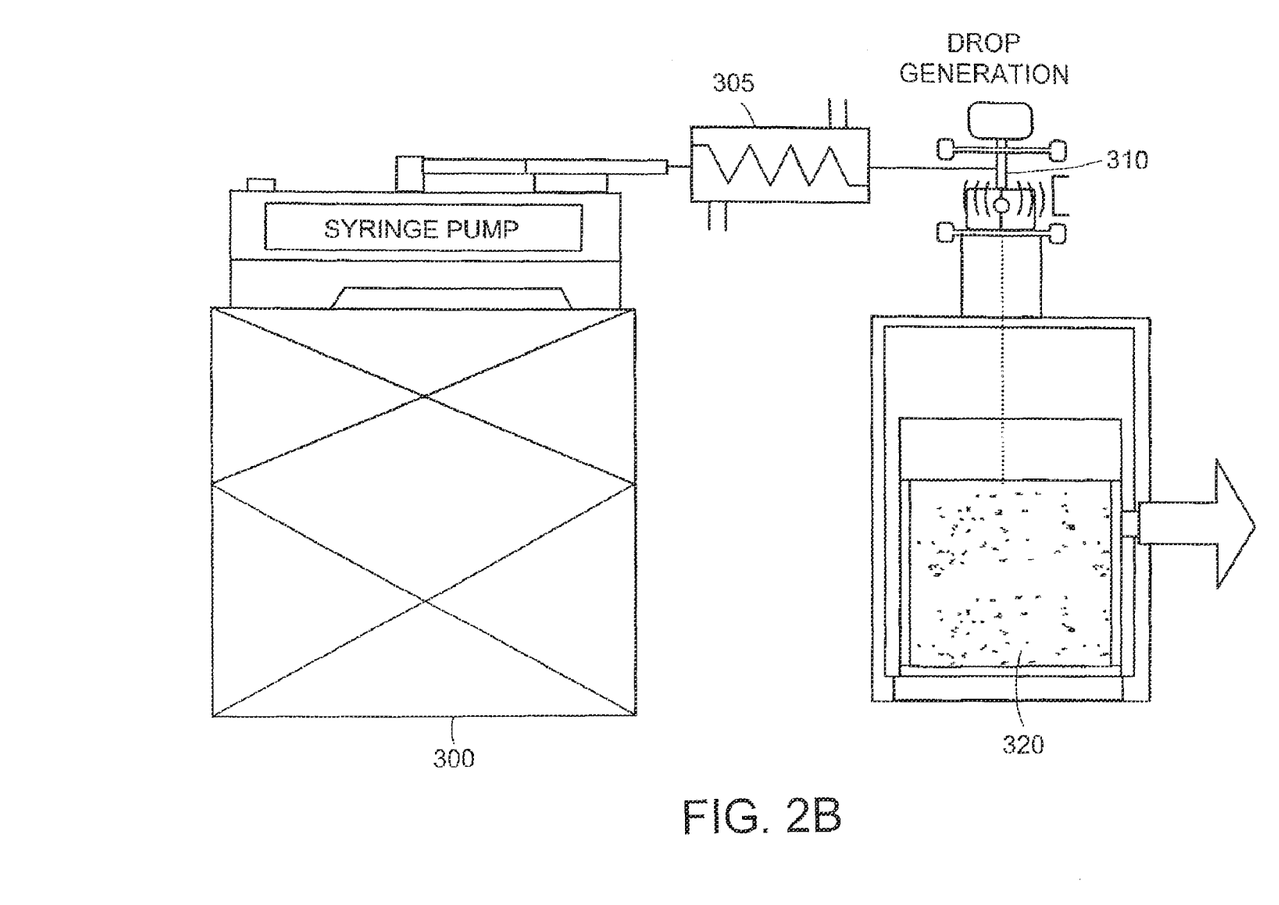
FIG. 2B is an enlarged schematic of region 2B in FIG. 2A.

FIG. 2A shows an embodiment of a system for producing particle 10. The system includes a flow controller 300, a drop generator 310, a gelling vessel 320, a reactor vessel 330, a gel dissolution chamber 340 and a filter 350. As shown in FIG. 2B, flow controller 300 delivers a solution that contains the material of matrix 12 (e.g., one or more polymers) and a gelling precursor (e.g., alginate) to a viscosity controller 305, which heats the solution to reduce viscosity prior to delivery to drop generator 310. The solution passes through an orifice in a nozzle in drop generator 310, forming drops of the solution. The drops are then directed into gelling vessel 320, where the drops contact a gelling agent (e.g., calcium chloride) and are stabilized by gel formation. The gel-stabilized drops are transferred from gelling vessel 320 to reactor vessel 330, where the polymer in the gel-stabilized drops is reacted (e.g., cross-linked), forming precursor particles. The precursor particles are transferred to gel dissolution chamber 340, where the gelling precursor is removed. The particles are then filtered in filter 350 to remove debris, and are sterilized and packaged as an embolic composition including the particles. Methods of making particles are described, for example, in U.S. patent application Ser. No. 10/637,130, filed on Aug. 8, 2003, and entitled "Embolization", which is incorporated herein by reference.

In some embodiments in which a drop generator is used in the preparation of particle 10, material 14 is included in the solution delivered by the drop generator, and the solution is processed as described above to form particle 10. In certain embodiments in which a drop generator is used in the preparation of particle 10, material 14 is included in the gelling vessel so that material 14 is incorporated into the drop when the drop contacts the gelling agent. Combinations of these methods can be used.

In some embodiments, material 14 is added to particle 10 in a separate operation. For example, material 14 can be applied to the surface of particle 10 by compounding matrix material 12 with one or more of the coating materials (described below) and then applying the compounded coating material to the surface of particle 10. In certain embodiments, material 14 can be placed in particle 10 (e.g., in one or more pores 16 or cavities of particle 10). In embodiments in which material 14 is in liquid form (e.g., a contrast agent) prior to being incorporated into particle 10, material 14 can be incorporated into the particles by, for example, absorption. Combinations of these methods can be used. For example, in some embodiments, one material can be incorporated into a cavity in a particle, while another material (either the same as, or different from, the first material) can be absorbed through the surface of the particle.

In some embodiments, multiple particles are combined with a carrier fluid (e.g., a saline solution, a contrast agent, or both) to form an embolic composition. Such embolic compositions can be used in, for example, neural, pulmonary, and/or AAA (abdominal aortic aneurysm) applications. The compositions can be used in the treatment of, for example, fibroids, tumors, internal bleeding, arteriovenous malformations (AVMs), and/or hypervascular tumors. The compositions can be used as, for example, fillers for aneurysm sacs, AAA sac (Type II endoleaks), endoleak sealants, arterial sealants, and/or puncture sealants, and/or can be used to provide occlusion of other lumens such as fallopian tubes. Fibroids can include uterine fibroids which grow within the uterine wall (intramural type), on the outside of the uterus (subserosal type), inside the uterine cavity (submucosal type), between the layers of broad ligament supporting the uterus (interligamentous type), attached to another organ (parasitic type), or on a mushroom-like stalk (pedunculated type). Internal bleeding includes gastrointestinal, urinary, renal and varicose bleeding. AVMs are for example, abnormal collections of blood vessels, e.g. in the brain, which shunt blood from a high pressure artery to a low pressure vein, resulting in hypoxia and malnutrition of those regions from which the blood is diverted. In some embodiments, a composition containing the particles can be used to prophylactically treat a condition.

The magnitude of a dose of an embolic composition can vary based on the nature, location and severity of the condition to be treated, as well as the route of administration. A physician treating the condition, disease or disorder can determine an effective amount of embolic composition. An effective amount of embolic composition refers to the amount sufficient to result in amelioration of symptoms or a prolongation of survival of the subject. The embolic compositions can be administered as pharmaceutically acceptable compositions to a subject in any therapeutically acceptable dosage, including those administered to a subject intravenously, subcutaneously, percutaneously, intratracheally, intramuscularly, intramucosaly, intracutaneously, intra-articularly, orally or parenterally.

An embolic composition can be prepared in calibrated concentrations of the particles for ease of delivery by the physician. Suspensions of the particles in saline solution can be prepared to remain stable (e.g., to not precipitate) over a duration of time. A suspension of the particles can be stable, for example, for from about one minute to about 20 minutes (e.g. from about one minute to about ten minutes, from about two minutes to about seven minutes, from about three minutes to about six minutes). The concentration of particles can be determined by adjusting the weight ratio of the particles to the physiological solution. If the weight ratio of the particles is too small, then too much liquid could be injected into a blood vessel, possibly allowing the particles to stray into lateral vessels. In some embodiments, the physiological solution can contain from about 0.01 weight percent to about 15 weight percent of the particles. A composition can include a mixture of particles, such as particles including ferromagnetic material, and particles including radiopaque material.

Figure 3A:
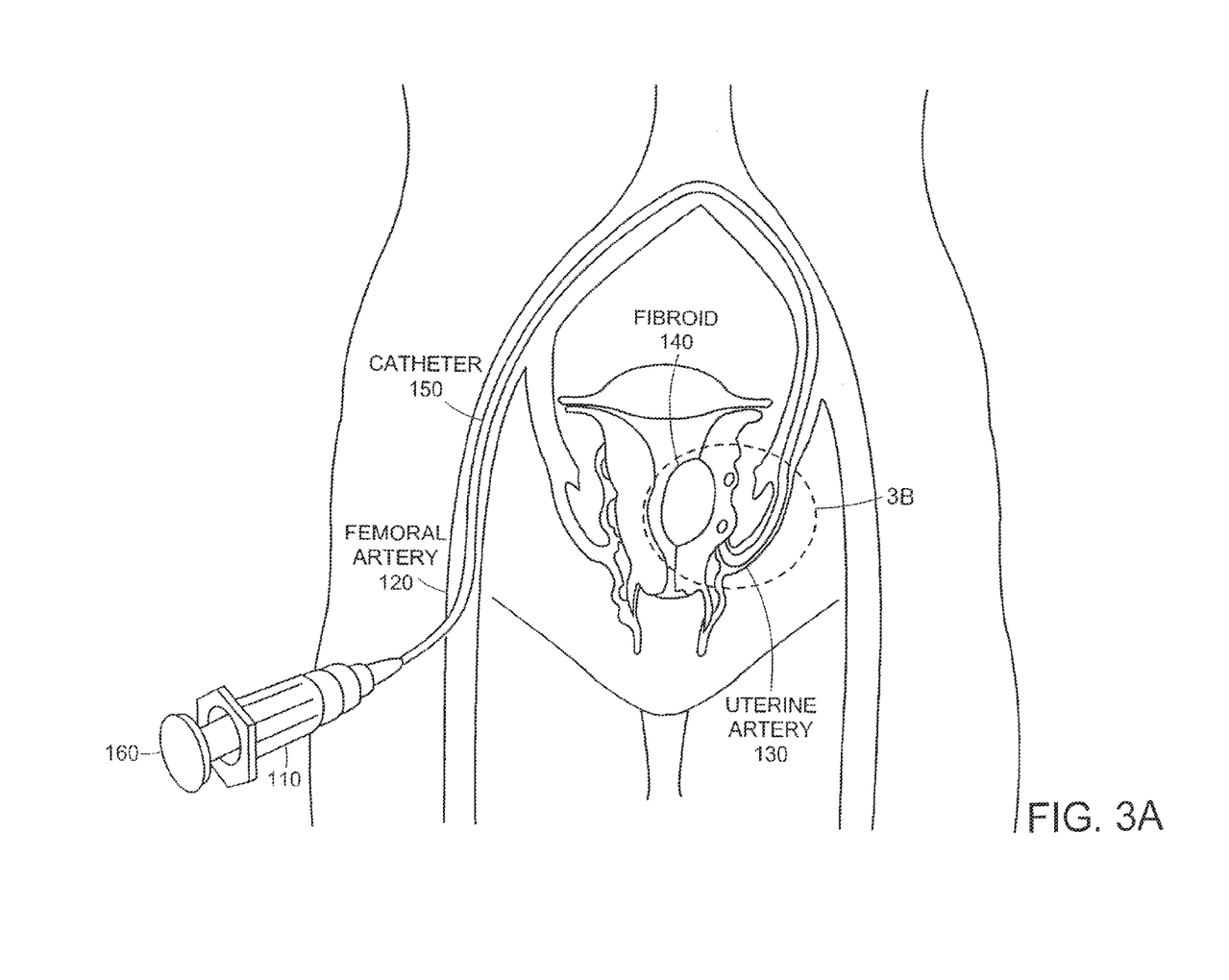
FIG. 3A is a schematic illustrating an embodiment of injection of an embolic composition including embolic particles into a vessel.
Figure 3B:
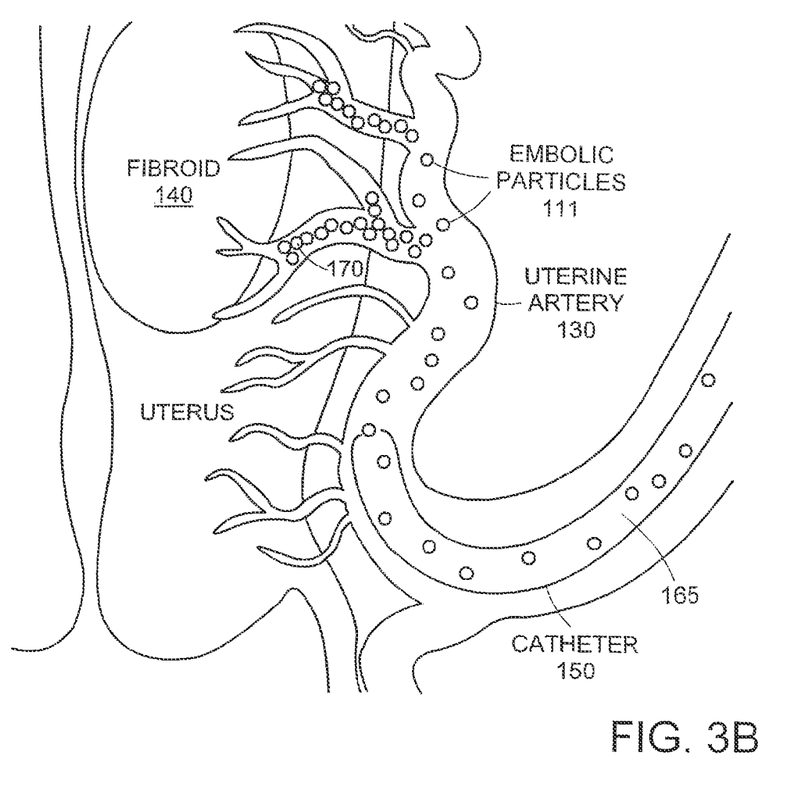
FIG. 3B is an enlarged view of the region 3B in FIG. 3A.

Referring to FIGS. 3A and 3B, an embolic composition, including embolic particles 111 and a carrier fluid, is injected into a vessel through an instrument such as a catheter 150. Catheter 150 is connected to a syringe barrel 110 with a plunger 160. Catheter 150 is inserted, for example, into a femoral artery 120 of a subject. Catheter 150 delivers the embolic composition to, for example, occlude a uterine artery 130 leading to a fibroid 140. Fibroid 140 is located in the uterus of a female subject. The embolic composition is initially loaded into syringe 110. Plunger 160 of syringe 110 is then compressed to deliver the embolic composition through catheter 150 into a lumen 165 of uterine artery 130.

Referring particularly to FIG. 3B, which is an enlarged view of section 3B of FIG. 3A, uterine artery 130 is subdivided into smaller uterine vessels 170 (e.g., having a diameter of about two millimeters or less) which feed fibroid 140. The embolic particles 111 in the embolic composition partially or totally fill the lumen of uterine artery 130, either partially or completely occluding the lumen of the uterine artery 130 that feeds uterine fibroid 140.

In some embodiments, among the particles delivered to a subject in an embolic composition, the majority (e.g., about 50 percent or more, about 60 percent or more, about 70 percent or more, about 80 percent or more, about 90 percent or more) of the particles have a diameter of about 3,000 microns or less (e.g., about 2,500 microns or less; about 2,000 microns or less; about 1,500 microns or less; about 1,200 microns or less; about 900 microns or less; about 700 microns or less; about 500 microns or less; about 400 microns or less; about 300 microns or less; about 100 microns or less) and/or about ten microns or more (e.g., about 100 microns or more; about 300 microns or more; about 400 microns or more; about 500 microns or more; about 700 microns or more; about 900 microns or more; about 1,200 microns or more; about 1,500 microns or more; about 2,000 microns or more; about 2,500 microns or more).

In certain embodiments, the particles delivered to a subject in an embolic composition have a mean diameter of about 3,000 microns or less (e.g., about 2,500 microns or less; about 2,000 microns or less; about 1,500 microns or less; about 1,200 microns or less; about 900 microns or less; about 700 microns or less; about 500 microns or less; about 400 microns or less; about 300 microns or less; about 100 microns or less) and/or about ten microns or more (e.g., about 100 microns or more; about 300 microns or more; about 400 microns or more; about 500 microns or more; about 700 microns or more; about 900 microns or more; about 1,200 microns or more; about 1,500 microns or more; about 2,000 microns or more; about 2,500 microns or more). Exemplary ranges for the mean diameter of particles delivered to a subject include from about 100 microns to about 300 microns; from about 300 microns to about 500 microns; from about 500 microns to about 700 microns; and from about 900 microns to about 1,200 microns. In general, the particles delivered to a subject in an embolic composition have a mean diameter in approximately the middle of the range of the diameters of the individual particles, and a variance of about 20 percent or less (e.g. about 15 percent or less, about ten percent or less).

In some embodiments, the mean size of the particles delivered to a subject in an embolic composition can vary depending upon the particular condition to be treated. As an example, in embodiments in which the particles in an embolic composition are used to treat a liver tumor, the particles delivered to the subject can have a mean diameter of about 500 microns or less (e.g., from about 100 microns to about 300 microns; from about 300 microns to about 500 microns). As another example, in embodiments in which the particles in an embolic composition are used to treat a uterine fibroid, the particles delivered to the subject in an embolic composition can have a mean diameter of about 1,200 microns or less (e.g., from about 500 microns to about 700 microns; from about 700 microns to about 900 microns; from about 900 microns to about 1,200 microns).

While certain embodiments have been described, the invention is not so limited.

As an example, in some embodiments, a particle can contain combinations of different types of materials (e.g., one or more ferromagnetic materials and one or more radiopaque materials; one or more radiopaque materials and one or more MRI-visible materials; one or more ferromagnetic materials and one or more MRI-visible materials; one or more MRI-visible materials, one or more ferromagnetic materials, and one or more radiopaque materials).

As another example, a particle can be prepared (e.g., for use in an embolic composition) without removal of the gelling precursor (e.g. alginate). Such particles can be prepared, for example, using a drop generator as described above, but without removing the gelling precursor from the particle after cross-linking.

As an additional example, in some embodiments a particle can include one or more therapeutic agents (e.g., drugs). The therapeutic agent(s) can be in and/or on the particle. Therapeutic agents include agents that are negatively charged, positively charged, amphoteric, or neutral. Therapeutic agents can be, for example, materials that are biologically active to treat physiological conditions; pharmaceutically active compounds; gene therapies; nucleic acids with and without carrier vectors; oligonucleotides; gene/vector systems; DNA chimeras; compacting agents (e.g., DNA compacting agents); viruses; polymers; hyaluronic acid; proteins (e.g., enzymes such as ribozymes); cells (of human origin, from an animal source, or genetically engineered); stem cells; immunologic species; nonsteroidal anti-inflammatory medications; oral contraceptives; progestins; gonadotrophin-releasing hormone agonists; chemotherapeutic agents; and radioactive species (e.g., radioisotopes, radioactive molecules). Non-limiting examples of therapeutic agents include anti-thrombogenic agents; antioxidants; angiogenic and anti-angiogenic agents and factors; anti-proliferative agents (e.g., agents capable of blocking smooth muscle cell proliferation); anti-inflammatory agents; calcium entry blockers; antineoplastic/antiproliferative/anti-mitotic agents (e.g., paclitaxel, doxorubicin, cisplatin); antimicrobials; anesthetic agents; anticoagulants; vascular cell growth promoters; vascular cell growth inhibitors; cholesterol-lowering agents; vasodilating agents; agents which interfere with endogenous vasoactive mechanisms; and survival genes which protect against cell death. Therapeutic agents are described, for example, in co-pending U.S. patent application Ser. No. 10/615,276, filed on Jul. 8, 2003, and entitled "Agent Delivery Particle", which is incorporated herein by reference.

As a further example, in some embodiments a particle can be coated (e.g., with a bioabsorable material). For example, a particle can include a polyvinyl alcohol matrix polymer with a sodium alginate coating. The coating can contain, for example, one or more therapeutic agents. In certain embodiments, a particle can be coated to include a high concentration of one or more therapeutic agents and/or loaded into the interior of the particle. The surface can release an initial dosage of therapeutic agent after which the body of the particle can provide a burst release of therapeutic agent. The therapeutic agent on the surface can be the same as or different from the therapeutic agent in the body of the particle. The therapeutic agent on the surface can be applied by exposing the particle to a high concentration solution of the therapeutic agent. The therapeutic agent coated particle can include another coating over the surface the therapeutic agent (e.g., a degradable and/or bioabsorbable polymer which erodes when the particle is administered). The coating can assist in controlling the rate at which therapeutic agent is released from the particle. For example, the coating can be in the form of a porous membrane. The coating can delay an initial burst of therapeutic agent release. The coating can be applied by dipping or spraying the particle. The erodible polymer can be a polysaccharide (such as an alginate). In some embodiments, the coating can be an inorganic, ionic salt. Other erodible coatings include water soluble polymers (such as polyvinyl alcohol, e.g., that has not been cross-linked), biodegradable poly DL-lactide-poly ethylene glycol (PELA), hydrogels (e.g., polyacrylic acid, haluronic acid, gelatin, carboxymethyl cellulose), polyethylene glycols (PEG), chitosan, polyesters (e.g., polycaprolactones), and poly(lactic-co-glycolic) acids (e.g., poly(d-lactic-co-glycolic) acids). The coating can include therapeutic agent or can be substantially free of therapeutic agent. The therapeutic agent in the coating can be the same as or different from an agent on a surface layer of the particle and/or within the particle. A polymer coating, e.g. an erodible coating, can be applied to the particle surface in cases in which a high concentration of therapeutic agent has not been applied to the particle surface. In some embodiments, the coating can include a ferromagnetic material, a radiopaque material, and/or an MRI-visible material. Alternatively or in addition, the particle interior can include a ferromagnetic material, a radiopaque material, and/or an MRI-visible material. The coating can include a higher, equal, or lower concentration of ferromagnetic material, radiopaque material, and/or MRI-visible material relative to the particle interior. In some embodiments, the interior of the particle can include one type of material (e.g., a ferromagnetic material), while the coating includes a different type of material (e.g., a radiopaque material). Coatings are described, for example, in U.S. patent application Ser. No. 10/615,276, filed on Jul. 8, 2003, and entitled "Agent Delivery Particle", which is incorporated herein by reference.

As an additional example, in some embodiments one or more particles is/are substantially nonspherical. In some embodiments, particles can be shaped (e.g., molded, compressed, punched, and/or agglomerated with other particles) at different points in the particle manufacturing process. In some embodiments (e.g., where the matrix polymer is a polyvinyl alcohol and the gelling precursor is sodium alginate), after contacting the particles with the gelling agent but before cross-linking, the particles can be physically deformed into a specific shape and/or size. After shaping, the matrix polymer (e.g., polyvinyl alcohol) can be cross-linked, optionally followed by substantial removal of the gelling precursor (e.g., alginate). While substantially spherical particles are preferred, non-spherical particles can be manufactured and formed by controlling, for example, drop formation conditions. In some embodiments, nonspherical particles can be formed by post-processing the particles (e.g., by cutting or dicing into other shapes). Particle shaping is described, for example, in co-pending U.S. patent application Ser. No. 10/402,068, filed Mar. 28, 2003, and entitled "Forming a Chemically Cross-Linked Particle of a Desired Shape and Diameter", which is incorporated herein by reference.

As a further example, in some embodiments the particles can be used for tissue bulking. As an example, the particles can be placed (e.g., injected) into tissue adjacent to a body passageway. The particles can narrow the passageway, thereby providing bulk and allowing the tissue to constrict the passageway more easily. The particles can be placed in the tissue according to a number of different methods, for example, percutaneously, laparoscopically, and/or through a catheter. In certain embodiments, a cavity can be formed in the tissue, and the particles can be placed in the cavity. Particle tissue bulking can be used to treat, for example, intrinsic sphincteric deficiency (ISD), vesicoureteral reflux, gastroesophageal reflux disease (GERD), and/or vocal cord paralysis (e.g., to restore glottic competence in cases of paralytic dysphonia). In some embodiments, particle tissue bulking can be used to treat urinary incontinence and/or fecal incontinence. The particles can be used as a graft material or a filler to fill and/or to smooth out soft tissue defects, such as for reconstructive or cosmetic applications (e.g., surgery). Examples of soft tissue defect applications include cleft lips, scars (e.g., depressed scars from chicken pox or acne scars), indentations resulting from liposuction, wrinkles (e.g., glabella frown wrinkles), and soft tissue augmentation of thin lips. Tissue bulking is described, for example, in co-pending U.S. patent application Ser. No. 10/231,664, filed on Aug. 30, 2002, and entitled "Tissue Treatment", which is incorporated herein by reference.

As an additional example, in certain embodiments one or more ferromagnetic materials, one or more MRI-visible materials and/or one or more radiopaque materials can be nonhomogeneously distributed in a particle. As an example, the density of the ferromagnetic, MRI-visible and/or radiopaque material(s) can be higher in the center region of the particle than at the surface region of the particle. As another example, the density of the ferromagnetic, MRI-visible and/or radiopaque material(s) can be higher at the surface region of the particle than in the center region of the particle.

As another example, in certain embodiments a particle can have a cavity (a portion that is substantially devoid of a matrix material such as a matrix polymer) that has a diameter of at least about 50 microns (e.g., at least about 100 microns, at least about 150 microns). In some embodiments, such a cavity can contain one or more ferromagnetic materials, one or more MRI-visible materials and/or one or more radiopaque materials. In such embodiments, the ferromagnetic, MRI-visible and/or radiopaque material(s) can be nonhomogeneously distributed in the particle.

As a further example, in some embodiments one or more ferromagnetic materials, one or more MRI-visible materials and/or one or more radiopaque materials can be located at the surface of the particle. In such embodiments, the interior of the particle can be substantially devoid the ferromagnetic, MRI-visible and/or radiopaque material(s), or the interior of the particle can further include the ferromagnetic, MRI-visible and/or radiopaque material(s).

As an additional example, in certain embodiments one or more ferromagnetic materials, one or more MRI-visible materials and/or one or more radiopaque materials can be attached to the surface of a particle (e.g., via a chemical linker).

As another example, in some embodiments a particle can be formed with no pores and/or no cavities.

As a further example, in some embodiments a particle can be formed without pores (nonporous particle).

Other embodiments are in the claims.

What is claimed is:

1. A particle, comprising a polymeric matrix and a ferromagnetic material distributed in the polymeric matrix, wherein the particle has a diameter of about 3,000 microns or less, the particle has a center region with a certain density of large pores having a mean cross-section of 20 microns or more and a surface region with a certain density of large pores, and the density of large pores of the center region is greater than the density of large pores of the surface region.

2. The particle of claim 1, wherein the ferromagnetic material is selected from the group consisting of transition metals, metal alloys, and metal oxides.

3. The particle of claim 1, wherein the ferromagnetic material is selected from the group consisting of magnetite, nickel, cobalt, iron and Mu-metal.

4. The particle of claim 1, wherein the ferromagnetic material comprises magnetite.

5. The particle of claim 1, wherein the ferromagnetic material is selected from the group consisting of soft ferrites, rare-earth magnet alloys, and amorphous and non-earth alloys.

6. The particle of claim 1, wherein the ferromagnetic material is in the shape of at least one article selected from the group consisting of particles, fibers, flakes, and powders.

7. The particle of claim 6, wherein the article has a diameter of from about two microns to about 20 microns.

8. The particle of claim 1, wherein the ferromagnetic material is substantially homogeneously distributed throughout the polymeric matrix.

9. The particle of claim 1, wherein the polymeric matrix comprises a polysaccharide.

10. The particle of claim 1, wherein the polymeric matrix comprises a member selected from the group consisting of polyvinyl alcohols, polyacrylic acids, polymethacrylic acids, poly vinyl sulfonates, carboxymethyl celluloses, hydroxyethyl celluloses, substituted celluloses, polyacrylamides, polyethylene glycols, polyamides, polyureas, polyurethanes, polyesters, polyethers, polystyrenes, polysaccharides, polylactic acids, polyethylenes, polymethylmethacrylates, polycaprolactones, polyglycolic acids, poly(lactic-co-glycolic) acids, and combinations thereof.

11. The particle of claim 1, wherein the particle further comprises a therapeutic agent.

12. The particle of claim 1, wherein the polymeric matrix comprises a first polymer and a second polymer.

13. The particle of claim 12, wherein the second polymer forms a coating over the first polymer.

14. The particle of claim 1, wherein the particle is substantially spherical.

15. The particle of claim 1, wherein the particle comprises from about 0.1 percent to about 90 percent by weight of the ferromagnetic material.

16. The particle of claim 1, wherein the polymeric matrix has a coating comprising an inorganic, ionic salt.

17. A method, comprising: heating a plurality of particles disposed in a body lumen, wherein the particles comprise a polymeric matrix and a ferromagnetic material distributed in the polymeric matrix, the particles have a diameter of 3,000 microns or less, and the particles have a center region with a certain density of large pores having a mean cross-section of 20 microns or more and a surface region with a certain density of large pores, and the density of large pores in the center region is greater than the density of large pores of the surface region.

18. The method of claim 17, wherein the method ablates body tissue.

19. The method of claim 17, wherein heating the particles comprises exposing the particles to RF radiation.

20. The method of claim 17, wherein heating the particles heats body tissue.

* * * * *